(12) United States Patent
Ganton et al.

(10) Patent No.: US 10,405,800 B2
(45) Date of Patent: Sep. 10, 2019

(54) METHODS, SYSTEMS, AND APPARATUSES FOR DETECTING ACTIVATION OF AN ELECTRONIC DEVICE

(71) Applicant: Capsule Technologies, Inc., San Diego, CA (US)

(72) Inventors: Robert Ganton, San Diego, CA (US); Robert Ballam, Eatons Hill (AU); Eugene Dantsker, San Diego, CA (US)

(73) Assignee: CAPSULE TECHNOLOGIES, INC., San Diego, CA (US)

( * ) Notice: Subject to any disclaimer, the term of this patent is extended or adjusted under 35 U.S.C. 154(b) by 179 days.

(21) Appl. No.: 15/379,313

(22) Filed: Dec. 14, 2016

(65) Prior Publication Data

US 2018/0014787 A1 Jan. 18, 2018

Related U.S. Application Data

(60) Provisional application No. 62/361,594, filed on Jul. 13, 2016.

(51) Int. Cl.
*A61B 5/00* (2006.01)
*H01H 47/00* (2006.01)
(Continued)

(52) U.S. Cl.
CPC .......... *A61B 5/6885* (2013.01); *A61B 5/0006* (2013.01); *A61B 5/0022* (2013.01);
(Continued)

(58) Field of Classification Search
CPC . A61B 5/6885; A61B 5/14865; A61B 5/0424; A61B 5/0006; A61B 5/0408;
(Continued)

(56) References Cited

U.S. PATENT DOCUMENTS 6,025,782 A 2/2000 Newham
8,088,096 B2 * 1/2012 Lauchard ............... A61M 5/20
604/66
(Continued)

FOREIGN PATENT DOCUMENTS

EP 2464008 A1 6/2012
EP 3000497 A2 * 3/2016 ............. A61B 90/36
(Continued)

OTHER PUBLICATIONS

International Search Report and Written Opinion—PCT/US2017/037192—ISA/EPO—dated Dec. 1, 2017.
(Continued)

*Primary Examiner* — Jared Fureman
*Assistant Examiner* — Michael J Warmflash
(74) *Attorney, Agent, or Firm* — Kilpatrick Townsend & Stockton LLP

(57) ABSTRACT

Disclosed are devices and methods for detecting activation of an electronic device, including a biomedical and biometric device. The electronic device can operate in a low-power mode until it is determined that the electronic device is in close proximity to or in contact with a body, and activated. The electronic device can include a first sensor including a first capacitance sensor, a second sensor, and a controller coupled to the first sensor and the second sensor. The controller can receive a first signal from the first sensor and determine that the electronic device is in close proximity to or in contact with a body based on the first signal, and receive a second signal from the second sensor and determine that the electronic device is activated based on one or both of the first signal and the second signal. The electronic device can transition from the low-power mode to an active mode in response to determining that the electronic device is activated.

25 Claims, 11 Drawing Sheets

(51) Int. Cl.
*A61B 5/0408* (2006.01)
*A61B 5/053* (2006.01)
*A61B 5/145* (2006.01)
*G01V 3/02* (2006.01)
*H03K 17/955* (2006.01)
*H03K 17/96* (2006.01)
*A61B 5/0424* (2006.01)
*A61B 5/1486* (2006.01)

(52) U.S. Cl.
CPC .......... *A61B 5/0408* (2013.01); *A61B 5/0424* (2013.01); *A61B 5/0538* (2013.01); *A61B 5/14532* (2013.01); *A61B 5/14865* (2013.01); *A61B 5/6848* (2013.01); *G01V 3/02* (2013.01); *H01H 47/002* (2013.01); *H03K 17/955* (2013.01); *H03K 17/962* (2013.01); *A61B 2560/0209* (2013.01); *A61B 2560/0219* (2013.01); *A61B 2562/028* (2013.01); *A61B 2562/0209* (2013.01); *A61B 2562/0214* (2013.01); *A61B 2562/0257* (2013.01); *H03K 2217/94036* (2013.01); *H03K 2217/94042* (2013.01); *H03K 2217/94089* (2013.01); *H03K 2217/960715* (2013.01)

(58) Field of Classification Search
CPC ... A61B 5/0538; A61B 5/6848; A61B 5/0022; A61B 5/14532; A61B 2560/0209; A61B 2560/0219; A61B 2562/0214; A61B 2562/028; A61B 2562/0257; A61B 2562/0209; H03K 17/955; H03K 17/962; H03K 2217/94036; H03K 2217/94089; H03K 2217/960715; H01H 47/002; G01V 3/02
See application file for complete search history.

(56) References Cited

U.S. PATENT DOCUMENTS

| | | | |
|---|---|---|---|
| 8,147,446 B2* | 4/2012 | Yodfat | A61M 5/14248 604/131 |
| 8,823,490 B2* | 9/2014 | Libbus | A61B 5/0006 340/6.1 |
| 8,998,842 B2 | 4/2015 | Lauchard et al. | |
| 9,017,255 B2 | 4/2015 | Raptis et al. | |
| 2008/0232604 A1* | 9/2008 | Dufresne | A61B 5/061 381/67 |
| 2009/0030285 A1 | 1/2009 | Andersen | |
| 2010/0021947 A1* | 1/2010 | Emery | A61B 5/14532 435/14 |
| 2012/0176179 A1* | 7/2012 | Harders | H03K 17/962 327/517 |
| 2014/0088454 A1 | 3/2014 | Mack | |
| 2015/0018900 A1 | 1/2015 | Kirk et al. | |
| 2015/0292856 A1* | 10/2015 | Ganton | A61B 5/6833 324/671 |

FOREIGN PATENT DOCUMENTS

| | | |
|---|---|---|
| WO | WO-2009016635 A2 | 2/2009 |
| WO | WO-2009148624 A1 | 12/2009 |
| WO | WO-2010077851 A2 | 7/2010 |

OTHER PUBLICATIONS

Partial International Search Report—PCT/US2017/037192—ISA/EPO—dated Aug. 31, 2017.
International Preliminary Report on Patentability—PCT/US2017/037192, The International Bureau of WIPO—Geneva, Switzerland, dated Sep. 27, 2018.

* cited by examiner

METHODS, SYSTEMS, AND APPARATUSES FOR DETECTING ACTIVATION OF AN ELECTRONIC DEVICE

CROSS-REFERENCE TO RELATED APPLICATIONS

This disclosure claims priority to U.S. Provisional Patent Application No. 62/361,594, filed Jul. 13, 2016, and entitled "METHODS, SYSTEMS, AND DEVICES FOR DETECTING PROXIMITY TO A BODY," which is hereby incorporated by reference in its entirety and for all purposes.

TECHNICAL FIELD

This disclose relates generally to detecting activation of an electronic device using a plurality of sensors, and more particularly, to a low-power sequence for detecting when an electronic device is in use, in contact with a body, and/or in proximity to a body using the plurality of sensors.

DESCRIPTION OF RELATED TECHNOLOGY

Electronic devices, including wearable medical devices or patches, may include various electronic components for biometric and biomedical applications. For example, an electronic sensor patch may be configured to transmit signals indicative of a sensed state, condition, or quantity. The signals generated by the electronic sensor patch may be processed to measure one or more detectable physical quantities based on a correlation between the signal and the underlying physical quantity. Non-limiting examples of sensors that may be implemented in an electronic sensor patch include temperature sensors, pulse sensors, electric field sensors (e.g., electroencephalograph sensors), moisture sensors, liquid flow sensors, magnetic sensors, piezoelectric sensors, pressure sensors, optical sensors, chemical sensors (e.g., blood glucose sensors), and other biomedical sensors.

Many electronic devices require a battery such that power management of the battery needs to be strategically controlled. Power management of the electronic device is important when the electronic device is not in active use, such as when the electronic device is being manufactured (e.g., factory mode) or stored (e.g., shelf mode). Power can be strategically managed to conserve battery life during factory and shelf modes and function in a low-power mode. Challenges in power management of electronic devices include proper detection of when the electronic device is in active use and no longer in a factory mode or shelf mode. Additional challenges in power management exist for detecting activation and proper use or installation of various components of the electronic device.

In many conventional electronic devices, an on/off switch can be provided to determine when the electronic device has been activated. However, an on/off switch may be inadvertently turned on that results in wasteful consumption of battery life, and an on/off switch may be inadvertently turned off to defeat the function of the electronic device. For example, an electronic patch may be inadvertently turned off to defeat the diagnostic function of the electronic patch. If electronic devices are packaged in the "on" position, battery life can be consumed quickly and the lifetime of the electronic device can be limited.

Sensors may be used with the electronic devices to determine if the electronic devices have been unpackaged, installed, placed on, or in use with a person. Determining that electronic devices are in use can provide valuable information for various purposes. Capacitance sensor technology may be used to determine if the electronic devices have met one or more specified conditions. Determining that the electronic devices are in use can provide valuable information, and determining that the electronic devices are not in use can trigger reduction in power consumption.

SUMMARY

The devices and methods of this disclosure each have several aspects, no single one of which is solely responsible for the desirable attributes disclosed herein.

One aspect of the subject matter of this disclosure can be implemented in an electronic device. The electronic device includes a first sensor where the first sensor includes a first capacitance sensor, a second sensor where the second sensor includes at least one of a capacitance sensor, an impedance sensor, an ohmic sensor, a mechanical switch, or any combination thereof, and a controller coupled to the first sensor and the second sensor. The controller is configured to receive a first signal from the first sensor, determine whether the device is in close proximity to or in contact with a body based on the first signal, receive a second signal from the second sensor in response to determining that the device is in close proximity to or in contact with the body, and determine whether the electronic device is activated based on one or both of the first signal and the second signal.

In some implementations, the electronic device further includes one or more needles capable of piercing through skin of the body, where the one or more needles include the second sensor. In some implementations, the second sensor includes a second capacitance sensor, and the controller is further configured to energize the one or more needles to charge the second capacitance sensor, and measure a rate of capacitance charge of the second capacitance sensor, where the second signal received from the second sensor includes the capacitance charge rate. In some implementations, the controller is further configured to energize the first sensor to charge the first capacitance sensor and measure a rate of capacitance charge of the first capacitance sensor, where the first signal received from the first sensor includes the capacitance charge rate. In some implementations, the electronic device further includes a housing and a base disposed on the housing, where the housing includes a circuit board and the first sensor. In some implementations, one or both of the housing and the base are rigid. In some implementations, the first sensor includes a first conductive surface and the second sensor includes a second conductive surface, each conductive surface being positioned on a surface of the housing configured to face the body and capable of being energized. In some implementations, the controller is further configured to set the set the electronic device to a low-power mode, and cause the electronic device to transition from the low-power mode to an active mode in response to determining that the electronic device is activated.

Another innovative aspect of the subject matter described in this disclosure can be implemented in an electronic device. The electronic device includes a first active node having a first conductive surface, a second active node having a second conductive surface, and a controller coupled to the first active node and the second active node. The first conductive surface is separated from the second conductive surface by an electrically insulating layer, and each of the first conductive surface and the second conductive surface is positioned on a side of the electronic device configured to contact a body. The controller is configured to receive a first measurement from the first active node, determine that the electronic device is in close proximity to or in contact with the body based on the first measurement, receive a second measurement from the second active node in response to determining that the electronic device is in close proximity to or in contact with the body, and determine that the electronic device is activated based on one or both of the first measurement and the second measurement.

In some implementations, the electrically insulating layer is connected to a ground node. In some implementations, the first conductive surface, the second conductive surface, and the electrically insulating layer are coplanar. In some implementations, the first active node includes a first capacitance sensor, and the controller is further configured to energize the first active node to charge the first capacitance sensor, receive the first measurement from the first active node where the first measurement indicates a rate of capacitance charge of the first capacitance sensor, and determine that the electronic device is in close proximity to or in contact with the body when the first measurement is greater than a threshold value. In some implementations, the electronic device further includes a capacitive touch sensor positioned on a side of the electronic device configured to face away from the body, where the controller is coupled to the capacitive touch sensor and is configured to receive a third measurement from the capacitive touch sensor, and determine whether the electronic device is activated based on the first measurement, the second measurement, the third measurement, or any combination thereof, the third measurement indicating that the capacitive touch sensor has been pressed for a sufficient duration.

Another innovative aspect of the subject matter described in this disclosure can be implemented in an electronic device. The electronic device includes a first means for sensing proximity to or contact with a body, where the first sensing means includes a first capacitance sensor, and a second means for sensing proximity to or contact with a body, wherein the second sensing means includes at least one of a capacitance sensor, an impedance sensor, an ohmic sensor, a mechanical switch, or any combination thereof. The electronic device further includes a means for controlling the electronic device coupled to the first sensing means and the second sensing means, where the controlling means is configured to receive a first signal from the first sensing means, determine whether the electronic device is in close proximity to or in contact with the body based on the first signal, receive a second signal from the second sensing means in response to determining that the electronic device is in close proximity to or in contact with the body, and determine whether the electronic device is activated based on one or both of the first signal and the second signal.

In some implementations, the electronic device further includes means for piercing the skin of the body, where the piercing means includes the second sensing means. In some implementations, the second sensing means includes a second capacitance sensor, and the controlling means is further configured to energize the piercing means to charge the second capacitance sensor, and measure a rate of capacitance charge of the second capacitance sensor, where the second signal received from the second sensing means includes the capacitance charge rate. In some implementations, the controlling means is further configured to energize the first sensing means to charge the first capacitance sensor, and measure a rate of capacitance charge of the first capacitance sensor, where the first signal from the first sensing means includes the capacitance charge rate. In some implementations, the electronic device further includes a housing and a base disposed on the housing, where the housing includes a circuit board and the first sensor, where one or both of the housing and the base are rigid.

Another innovative aspect of the subject matter described in this disclosure can be implemented in a method of an electronic device in a low-power mode for determining whether the electronic device is activated. The method includes receiving a first signal from a first sensor, determining that the electronic device is in close proximity to or in contact with a body based on the first signal, receiving a second signal from a second sensor in response to determining that the electronic device is in close proximity to or in contact with the body, determining that the electronic device is activated based on one or both of the first signal and the second signal, and causing the electronic device to transition from a low-power mode to an active mode in response to determining that the electronic device is activated and the electronic device being in the low-power mode.

In some implementations, the method further includes receiving a third signal from a third sensor, and determining whether the electronic device is activated based on the first signal, the second signal, the third signal, or any combination thereof, wherein the electronic device is caused to transition from the low-power mode to the active mode in response to determining and determining that the electronic device is activated and the electronic device being in the low-power mode. In some implementations, the first sensor includes a first capacitance sensor, where the first signal received from the first sensor includes a measurement of the rate of capacitance charge of the first capacitance sensor. In some implementations, the method further includes setting the electronic device to a manufacturing mode, and determining that a duration of time has elapsed in the manufacturing mode, where the electronic device is set to a low-power mode after the duration of time has elapsed.

BRIEF DESCRIPTION OF THE DRAWINGS

The accompanying drawings, which are incorporated herein and constitute part of this specification, illustrate exemplary embodiments of the claims, and together with the general description given above and the detailed description given below, serve to explain the features of the claims.

Like reference numbers and designations in the various drawings indicate like elements.

DETAILED DESCRIPTION

Figure 1:
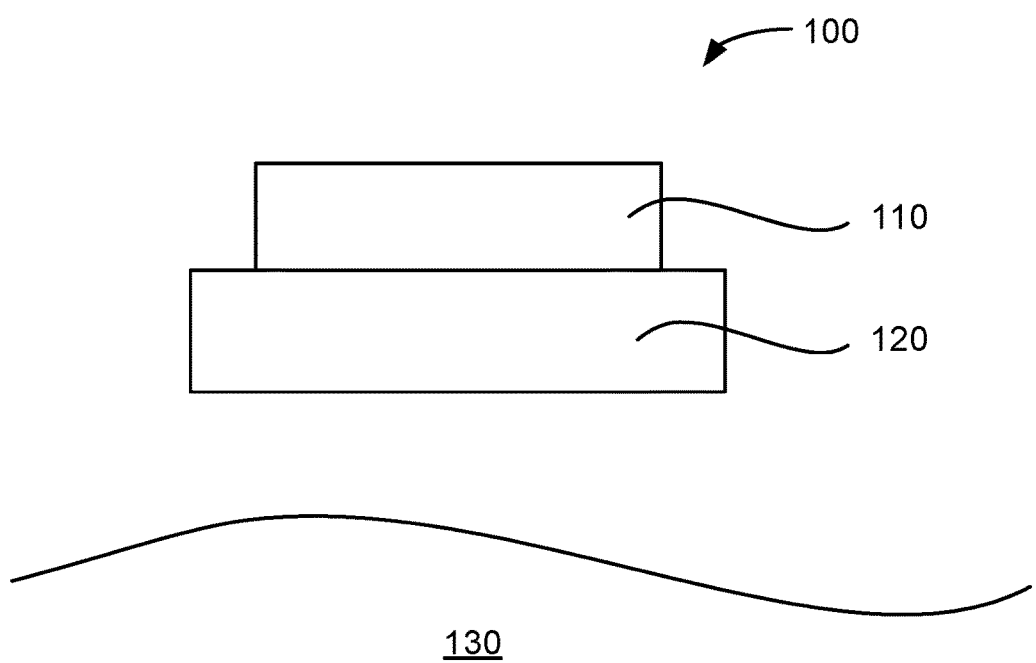
FIG. 1 is a schematic representation of an example electronic device including a housing and a base according to some implementations.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

The described implementations may be implemented in any device, apparatus, or system that includes a sensor system. As used herein, an "electronic device" and "electronic sensor device" may be used interchangeably. In some implementations, the electronic device may be a biomedical or biometric device. In some implementations, the electronic device may be a wearable device, such as an electronic patch worn by a user. Non-limiting examples of wearable devices include patches, bracelets, armbands, wristbands, rings, headbands, belts, etc. The electronic device can include one or more sensors for sensing or measuring detectable physical phenomena or quantities. The one or more sensors may be used to take readings or measurements of a patient's body, for example. The electronic device may be configured to transmit signals indicative of a measurement or sensed state, condition, or quantity. The signals generated by a sensor may be processed to measure the detectable physical phenomena or quantities based on a correlation between the signal and the underlying physical phenomenon or quantity. Non-limiting examples of sensors that may be implemented in an electronic device include temperature sensors, pulse sensors, electric field sensors (e.g., electroencephalograph sensors), moisture sensors, liquid flow sensors, magnetic sensors, piezoelectric sensors, pressure sensors, optical sensors, chemical sensors (e.g., blood glucose sensors), etc.

The present disclosure relates generally to devices and methods for detecting when an electronic device is in close proximity to a body, in contact with a body, and/or in use with a body using a plurality of sensors. The aforementioned plurality of sensors may be different than the sensors used to take readings or measurements of a patient's body. The sensors may detect, determine, and validate if an electronic device has been properly installed or activated. The sensors also may detect and validate if certain components or other sensors of the electronic device have been properly used or activated. In some implementations, the detection and validation can occur over a sequence of stages.

At least one of the sensors may be a capacitance sensor, where the capacitance sensor can indicate whether the electronic device is in close proximity to or in contact with a body. In some implementations, a controller in the electronic device is configured to cause the capacitance sensor to be charged and receive a signal from the capacitance sensor, where the signal includes a measurement of a rate of capacitance charge of the capacitance sensor. As a capacitor in a capacitance sensor charges up, the rise time or the time that it takes a circuit to reach a certain voltage can increase due to proximity to a patient's body. To validate that the electronic device has been properly installed or activated, additional sensors can provide further feedback to the controller of the electronic device. Such additional sensors can include at least one of a capacitance sensor, an impedance sensor, an ohmic sensor, a mechanical switch, or any combination thereof. Other additional sensors can include sensors used for taking readings or measurements of a patient's body, such as glucose sensors or electrocardiograph (EKG) electrodes. In some implementations, the electronic device can transition from a low-power mode to an active mode upon determining that the electronic device has been properly installed and/or activated.

In some implementations, two or more sensors include at least a first conductive surface and a second conductive surface that are positioned on a side of the electronic device configured to face/contact the body, where at least one of the sensors is a capacitance sensor. In some implementations, two or more active nodes of one or more sensors include at least a first conductive surface and a second conductive surface that are positioned on a side of the electronic device configured to face/contact the body, where at least one of the sensors is a capacitance sensor. The conductive surfaces may be separated by an electrically insulating layer. In some implementations, a first conductive surface may include an area around a perimeter of a second conductive surface. In some implementations, the electrically insulating layer, the first conductive surface, and the second conductive surface are coplanar. In some implementations, the electronic device further includes a capacitive touch sensor on a side of the electronic device configured to face away from the body. The sensor(s) with the first and second conductive surfaces can indicate whether the electronic device is in close proximity to or in contact with the body, and the capacitive touch sensor may provide validation that the electronic device is properly installed or activated.

Particular implementations of the subject matter described in this disclosure can be implemented to realize one or more of the following potential advantages. Multiple sensors can provide additional feedback to validate and reinforce that the electronic device is in use, thereby improving the reliability of the electronic device and reducing the likelihood of false detection. Moreover, multiple sensors can provide multiple stages of activating the electronic device, thereby giving a user more feedback across multiple stages of use. Using a capacitance sensor of the present disclosure that uses the measurement of a rate of capacitance charge can reduce the power consumption for detecting proximity or contact with a body. Such measurements can be periodically performed during a low-power mode to further reduce the power consumption. Additionally, such measurements can be performed quickly so as to limit power consumption during the detection operation. The sensors positioned on a side of the electronic device configured to face/contact the body have a geometry that can increase skin contact over a wide area and increase the likelihood of detection. The geometry also can be adjusted to adjust the sensitivity of detection. The sensor arrangement of the present disclosure can allow the electronic device to be encapsulated and sterilized before introduction to the user. Furthermore, the sensor arrangement can be incorporated in various types of devices, including devices with rigid, semi-rigid, or flexible circuitry and housing.

FIG. 1 is a schematic representation of an example electronic device including a housing and a base. An electronic device 100 may be applied to a patient, such as on skin of a patient's body 130. The electronic device 100 in FIG. 1 includes a housing 110 facing the patient's body 130 and a base 120 disposed on the housing 110. The base 120 can be disposed on a side of the housing 110 facing the patient's body 130. The housing 110 can serve as an electronic package that includes various circuitry, electronic components, sensors, and control systems. In some implementations, the housing 110 may include a circuit board and a sensor, where the circuit board includes a controller. The sensors may include, for example, ohmic or capacitive sensing technology. One or more sensors may be configured to determine whether the electronic device 100 is in close proximity to or in contact with the patient's body 130. Other sensors may assist in measuring detectable physical phenomena or other quantities, such as temperature, pulse rate, blood pressure, blood glucose levels, etc. A base 120 may be disposed on the housing 110, or vice versa, and may be capable of being detached from the housing 110. In some implementations, the base 120 can serve as a protective layer or cover for the housing 110. In some implementations, the base 120 includes electrically insulating material. For example, a user may grip the housing 110 and apply a removal force to remove the housing 110 from the base 120.

In some implementations, the electronic device 100 is an electronic patch or electronic sensor patch. The electronic patch may be suitable for performing various biometric or biomedical applications. The housing 110 in such implementations may be peeled off from the base 120, or the base 120 may be peeled off from the housing 110. A side of the housing 110 is exposed and may be affixed to the patient's body 130. After removal of the base 120 from the housing 110, the housing 110 of the electronic device 100 may be affixed to the patient's body 130 or other surface. One or more sensors in the electronic device 100 may be configured to detect when the base 120 has been removed and when the housing 110 of the electronic device 100 has been affixed to the patient's body 130. For instance, removal of the base 120 from the housing 110 may cause the electronic device 100 to transition from a low-power mode (e.g., shelf mode) to a high-power mode (e.g., active mode).

In some implementations, the electronic device 100 is not limited to an electronic patch or electronic sensor patch, but is any electronic device 100 that may be applied to or used with a patient's body 130. For example, the electronic device 100 is a device capable of biometric or biomedical functions, such as a glucometer, EKG monitor, blood pressure monitor, temperature sensor, or other device. Regardless of the shape, size, or structure of the electronic device 100, one or more sensors in the electronic device 100 may be capable of detecting when the electronic device 100 is in close proximity to or in contact with the patient's body 130.

In some implementations, the housing 110 may include one or more capacitance sensors covered by the base 120. Typically, the base 120 may cover the one or more capacitance sensors so that they would not be triggered by routine handling or inadvertent pressing. Once the base 120 is removed from the housing 110, then the housing 110 may be affixed to the patient's body 130 and the one or more capacitance sensors can detect whether the electronic device 100 is in contact with the patient's body 130. Alternatively, the base 120 covering a side of the housing 110 facing the patient's body 130 is not removed but may remain on the housing 110. A surface of the base 120 facing the patient's body 130 may attach to the patient's body while the base 120 covers the one or more capacitance sensors. The one or more capacitance sensors can detect whether the electronic device 100 is in close proximity to the patient's body 130 with the base 120 in place.

In some implementations, one or both of the housing 110 and the base 120 are rigid. For example, the housing 110 of the electronic device 100 may be rigid. In some implementations, one or both of the housing 110 and the base 120 are flexible. For example, the housing 110 of the electronic device 100 may be flexible. In some implementations, one or both of the housing 110 and the base 120 are semi-rigid. For example, the housing 110 of the electronic device 100 may be semi-rigid. With rigid or semi-rigid housing 110 and/or base 120, advantages of lower costs and ease of manufacturing may be achieved. Having the housing 110 and/or base 120 be rigid or semi-rigid can allow other parts of the electronic device 100 to also be rigid or semi-rigid, thereby simplifying assembly of the electronic device 100. With flexible housing 110 and/or base 120, an advantage of more effective adherence of the electronic device 100 to the patient's body 130 may be achieved.

Figure 2:
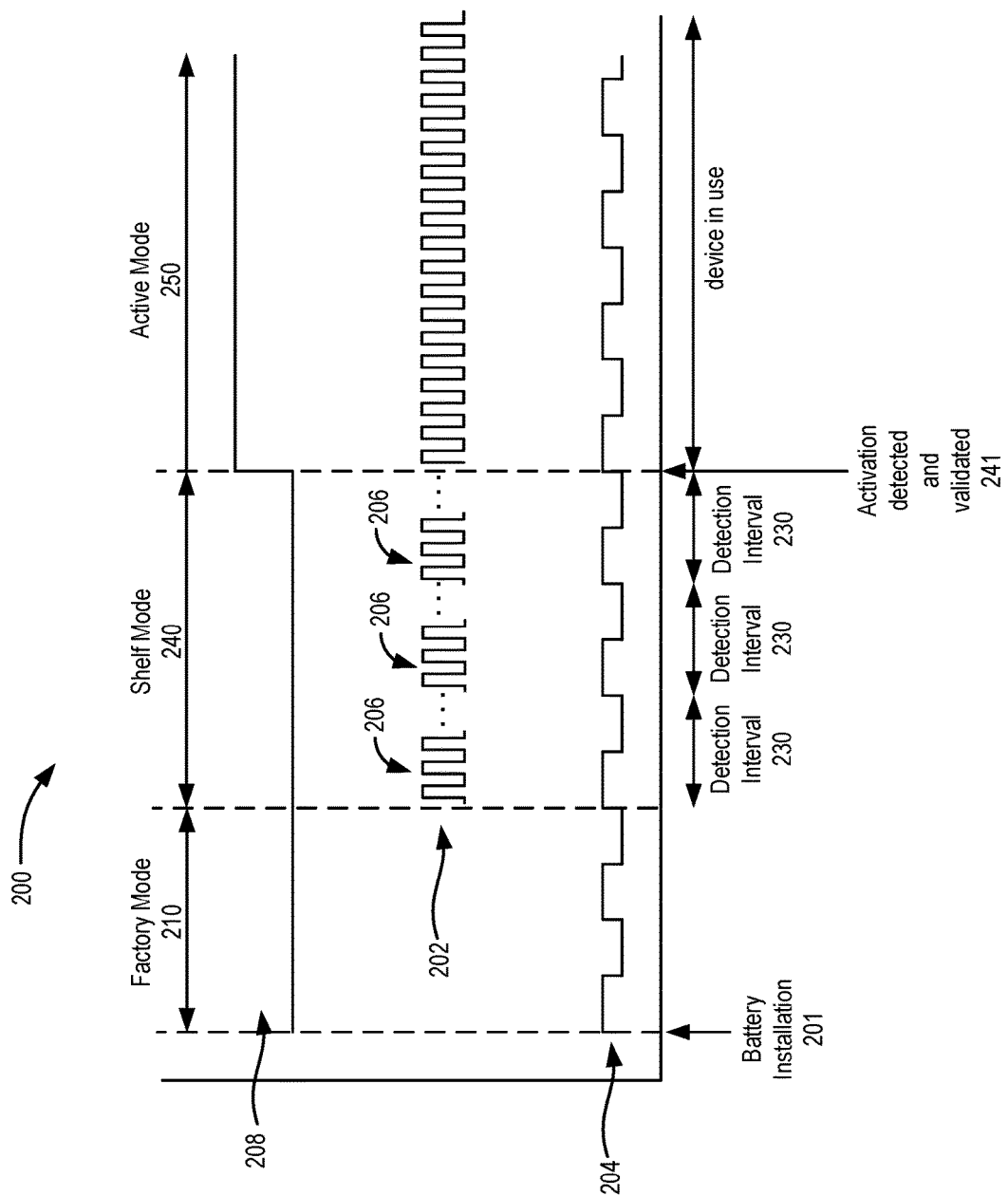
FIG. 2 is a timing diagram illustrating power consumption of various electronic components of an electronic device during a factory mode, a shelf mode, and an active mode according to some implementations.

An electronic device 100 may be capable of operating in different modes or power states to manage consumption of power. The electronic device 100 may transition from one mode to another depending on if certain conditions are met, such as whether certain timing conditions or attachment conditions are met. Different modes or power states can add greater range and flexibility for power management of the electronic device 100. By way of an example, the electronic device 100 can have a low-power mode and a high-power mode, or the electronic device 100 can have two or more of a lowest-power mode, a low-power mode, a high-power mode, and a highest-power mode. As shown in FIG. 2, an electronic device can have a lowest-power mode (e.g., factory mode), a low-power mode (e.g., shelf mode), and a high-power mode (e.g., active mode). It will be understood that the electronic device with two or more power states can have other power states.

FIG. 2 is a timing diagram illustrating power consumption of various electronic components of an electronic device during a factory mode, a shelf mode, and an active mode according to some implementations. A factory mode 210 may be a transient mode that allows for configuration, assembly, and/or testing of an electronic device. During a shelf mode 240, the electronic device is "active" in monitoring for certain conditions to be met, but operating in a low-power state to extend the shelf life of the electronic device. When the electronic device transitions from the shelf mode 240 to an active mode 250, the electronic device becomes fully operational.

To accomplish power management, a timing diagram 200 tracks power usage of certain components in the electronic device as the electronic device transitions between different modes 210, 240, and 250. In some implementations, the factory mode 210 may be established that represents a duration of time in the manufacturing process. For example, the factory mode 210 may be established from application of power, such as when a battery is installed at battery installation 201, and may continue until manufacturing, assembly, testing, and packaging is complete. Prior to the factory mode 210, the electronic device may be operating at an even lower power in which all components, including clocks and peripheral electronic components, are turned off. During the factory mode 210, a controller may begin operation of a low-power clock 204. All other components, including a high-power clock and peripheral electronic components, are turned off. The low-power clock 204 allows the controller to know the elapsed time since activation (e.g., battery installation 201) and to track a remaining time for the factory mode 210. When the factory mode 210 expires, the electronic device transitions to a shelf mode 240 in which detection operations are periodically performed. In the shelf mode 240, the electronic device can use the low-power clock 204 to periodically "wake up" one or more sensors to determine if the electronic device meets specified conditions, such as if the electronic device has been applied or attached.

A detection interval 230 may represent a brief interval of time in which one or more sensors sense whether specified conditions are met by the electronic device. The detection interval 230 may be performed cyclically until the electronic device meets the specified conditions. In some implementations, the detection interval 230 may range from a few seconds to a few minutes, such as between about 1 second and about 60 seconds. In other implementations, the detection interval 230 may be shorter or longer. The detection interval 230 may be set in order to optimize the responsiveness of the finished electronic device product. For example, the detection interval 230 may be set to optimize the length of a low-power state to preserve battery life, while providing a relatively short sensing interval for improved responsiveness.

During the detection interval 230, the controller may be configured to perform a check of the one or more sensors to determine if the specified conditions are met. In one example, a high-power clock 202, such as a full duty cycle clock, may be enabled for a period of time sufficient to complete detection operations. The high-power clock 202 may generate a full duty clock signal 206 for a sufficiently short period of time to detect if the specified conditions are met while having a minimal effect on power. The sufficiently short period of time of the full duty clock signal 206 may be in the range of a few microseconds to a few milliseconds, such as less than about 10 microseconds. During the full duty clock signal 206, the controller and one or more sensors may perform a detection operation or reading. The one or more sensors may generate a signal to be received by the controller. In some implementations, the one or more sensors may include a capacitance sensor that generates a signal indicating a rate of capacitance charge when the capacitance sensor is charged. This can be done by calculating capacitance from a time constant or by inferring the capacitance by changes in the amount of rise time associated with the signal. A longer charge cycle is generally associated with being in contact with a person or in close proximity to a person's skin. Upon receiving the signal indicating the rate of capacitance charge from the one or more sensors, the controller can determine if the specified conditions for detection are met. If the specified conditions are not met, the high-power clock 202 is disabled, and the one or more sensors and/or the controller return to sleep. In other words, the one or more sensors and/or the controller are disabled or turned off until the next detection interval 230. The low-power clock 204 continues to operate to periodically wake up the one or more sensors from sleep. If the specified conditions are met, the full capabilities of the electronic device may be turned on, including peripheral electronic components.

Determining that the specified conditions are met to transition from the shelf mode 240 to the active mode 250 may occur in response to activation detection and validation 241. Multiple sensors may be employed to determine if the electronic device is in close proximity to or in contact with a body, and validate that the electronic device is properly installed, activated, or in use. During the active mode 250, all sensors associated with the electronic device and peripheral electronic components may be activated. Sensors associated with the electronic device and peripheral electronic components may be activated sequentially according to a validation sequence using multiple sensors. Sensing components and wireless communications components 208 (e.g., radio-frequency modules) may be activated during the active mode 250. Furthermore, the high-power clock 202 may operate continuously or as may be called for under the control of the controller to perform sensor readings and to transmit the sensor readings to another device. The full operations of the electronic device may be available during the active mode 250. In some implementations, the low-power clock 204 may continue to be in use as shown in FIG. 2, or may be optionally disabled. The low-power clock 204 may monitor quantities like remaining battery charge state or remaining time-to-live. In some implementations, the electronic device may be removed from the body, taken away from close proximity to the body, uninstalled, deactivated, or removed from use. Under such conditions, the electronic device may return to a low-power mode or shelf mode 240. Alternatively or additionally, the electronic device may provide an alert or notification to another device, such as a smartphone, cloud server, or other remote device.

In some implementations, the electronic device may be provided with a total active life parameter, which may be influenced by quality or other factors. The total active life parameter may be in the form of a timer value, which, like other timer values, may be counted down by operation of the low-power clock 204. In some implementations, the total active life parameter may be counted down during the various modes 210, 240, and 250, such as during the shelf mode 240 and the active mode 250. When the total active life timer indicates that the electronic device is reaching the end of its active life, the electronic device may alert a user. In some implementations, the alert may indicate that the electronic device should be removed or replaced.

Figure 3A:
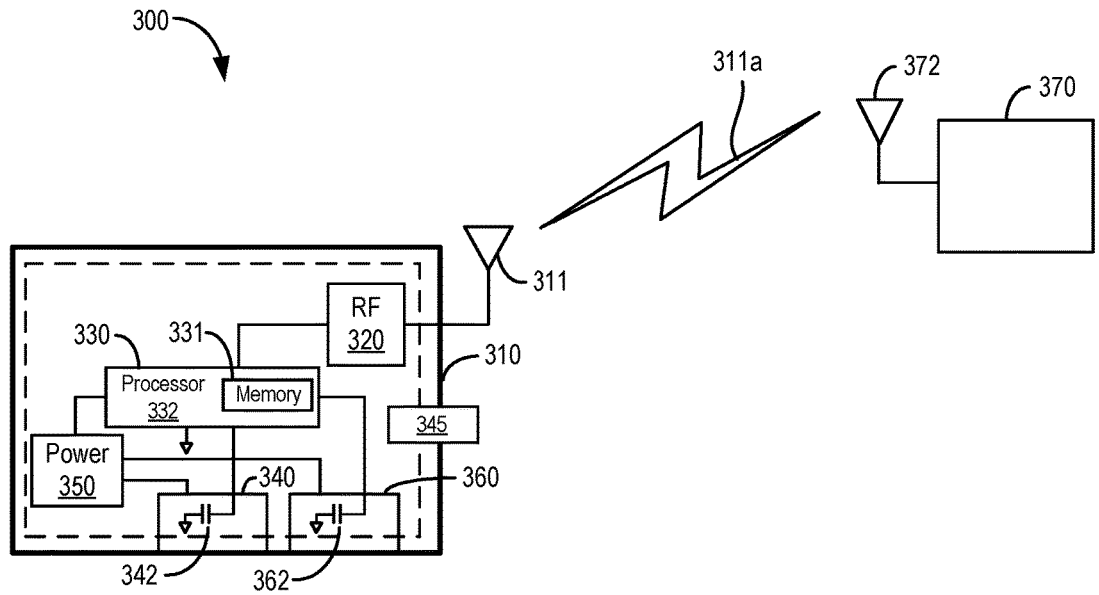
FIG. 3A is a block diagram representation of an example electronic device in communication with a remote device according to some implementations.

FIG. 3A is a block diagram representation of an example electronic device in communication with a remote device according to some implementations. An electronic device 300 can include an antenna 311, a wireless communications component 320, a controller 330, a first sensor 340 for detecting a first condition of the electronic device 300, a second sensor 360 for detecting a second condition of the electronic device 300, one or more sensors 345, and a power supply 350. Some or all of the components may be contained in a housing 310. As shown by the dotted line, some or all of the components of the electronic device 300 may be encapsulated or sealed to provide environmental protection. In some implementations, the electronic device 300 may be configured to operate in a variety of environmental conditions including wet conditions. Some or all of the components of the electronic device 300, such as the controller 330 and the wireless communications component 320, may be provided as individual components or may be integrated into a single device. The components of the electronic device 300 may be sealed or encapsulated to allow operation when at least partially submerged in water or other liquids.

In some implementations, the wireless communications component 320 includes a transmitter or transceiver to conduct one-way or two-way radio-frequency (RF) communication. The wireless communications component 320 may be an RF module that includes base band, intermediate and transmit frequency modules and encoders. The RF module may operate in one or more of a number of RF bands depending on the type of communications supported by the configuration of a remote device 370. The wireless communications component 320 may be coupled to the controller 330 and coupled to the antenna 311. The antenna 311 of the electronic device 300 may be configured to establish wireless communication with an antenna 372 of the remote device 370 via a wireless communication link 311a. Sensor data or readings from the one or more sensors 345 may be transferred from the electronic device 300 to another device. In addition, feedback regarding detection operations of the electronic device 300 may be communicated to the remote device 370, and the remote device 370 may be configured to provide instructions to the electronic device 300. For example, as the remote device 370 receives feedback regarding detection conditions being met by the electronic device 300, the remote device 370 may communicate a sequence of instructions for fully activating the electronic device 300. Thus, if the remote device 370 receives feedback that the first sensor 340 detects the first condition, then the remote device 370 may instruct a user to handle the electronic device 300 so that the second sensor 360 meets the second condition in order to fully activate the electronic device 300. Though not shown in FIG. 3A, the electronic device 300 may be equipped with additional sensors for detecting additional conditions, such as a third sensor for detecting a third condition, a fourth sensor for detecting a fourth condition, a fifth sensor for detecting a fifth condition, and so on. The first condition, second condition, third condition, and so forth can include conditions such as contact with a body, close proximity to a body, application of a needle, application of an electrode of an EKG monitor, pressing of a button, and detachment of a base, among other conditions. In some implementations, the remote device 370 is a smartphone, a cloud server, or any other device having cellular communication capability.

The controller 330 of the electronic device 300 may be capable of performing some or all of the methods described herein. The controller 330 may be used interchangeably with a "control unit," "control system," "microcontroller," or "processing unit." The controller 330 may include a processor 332 and a memory 331. The processor 332 may be a single or multi-core processor, which may be general purpose or specifically adapted for use in the electronic device 300. The memory 331 of the controller 330 may be volatile or non-volatile memory (e.g., flash memory) or a combination thereof. The memory 331 may provide instructions to the controller 330.

The one or more sensors 345 may be capable of sensing or measuring detectable physical phenomena or quantities, such as taking readings or measurements of a patient's body. Examples of the one or more sensors 345 may include temperature sensors, pulse sensors, electric field sensors (e.g., electroencephalograph sensors), moisture sensors, liquid flow sensors, magnetic sensors, piezoelectric sensors, pressure sensors, optical sensors, chemical sensors (e.g., blood glucose sensors), etc.

The controller 330, the first sensor 340, the second sensor 360, the wireless communications component 320, and any other electronic component of the electronic device 300 may be powered by the power supply 350. In some implementations, the power supply 350 is a battery. The battery may be any suitable battery of sufficient power to energize various circuits associated with the electronic device 300 over the projected lifetime of the electronic device 300. For example, the battery can be a standard watch or coin cell battery.

One or both of the sensors 340, 360 may include a capacitance sensor. In some implementations, the first sensor 340 includes a capacitance sensor 342 capable of having an effective capacitance and a resistance. In some implementations, the second sensor 360 includes a capacitance sensor 362 capable of having an effective capacitance and a resistance. However, it is understood that the second sensor 360 can be capable of other sensing mechanisms. The second sensor 360 can implement various sensing mechanisms that can include but are not limited to the examples discussed below. For example, the second sensor 360 can include a bioimpedance sensor that is capable of directly measuring the ohmic impedance of the skin of a patient's body 130 to determine detection of skin. In another example, the second sensor 360 can include an EKG electrode that is capable of using capacitive sensing or directly measuring impedance between two or more electrodes to determine if the electronic device 300 has been properly installed. In yet another example, the second sensor 360 can include a glucose monitor needle or sense wires to determine if a portion of the electronic device 300 has been injected into the skin of the patient's body 130. In still yet another example, the second sensor 360 can include a mechanical switch capable of being pressed by a user. The first sensor 340 and the second sensor 360 may be configured to detect conditions of the electronic device 300 to determine if the electronic device 300 is properly installed, activated, or in use.

Figure 3B:
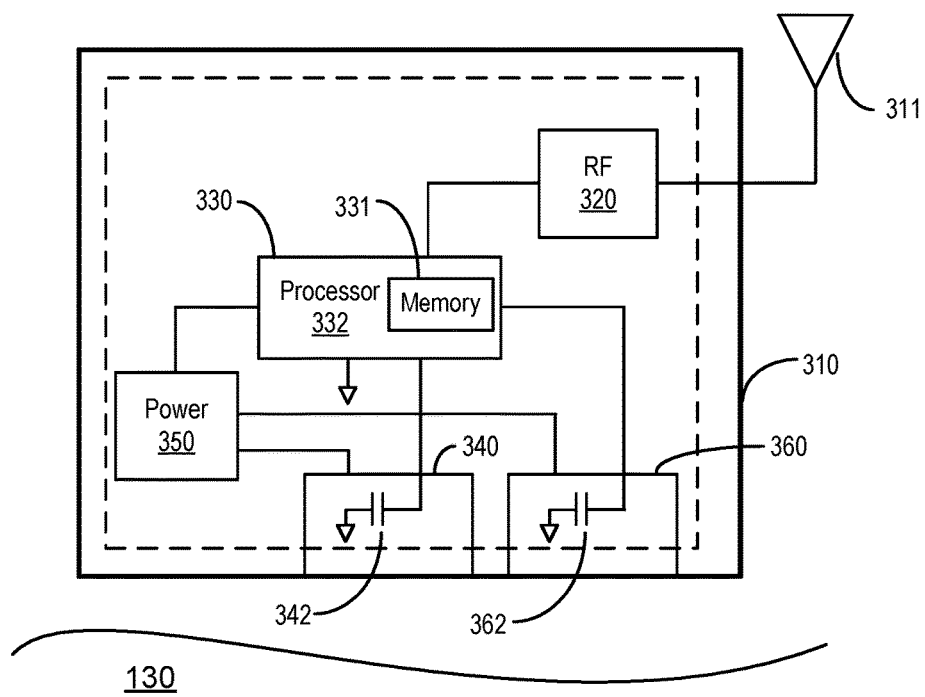
FIG. 3B is a block diagram representation of an example electronic device in proximity to a body according to some implementations.

FIG. 3B is a block diagram representation of an example electronic device in proximity to a body according to some implementations. When the electronic device 300 is in close proximity to or in contact with the body 130, then one or both of the sensors 340, 360 may be configured to determine that such a condition is met. One or both of the sensors 340, 360 may be able to differentiate between an inanimate object and the body 130 of a living organism. The controller 330 may be trained to differentiate between signals from the sensors 340, 360 indicative of an inanimate object or the body 130 of a living organism, such as a person. Generally, inanimate objects are not conductive enough to trigger a capacitance sensor in one or both of the sensors 340, 360. Moreover, the controller 330 may be trained to detect the body 130 of a person when the person is essentially in direct physical touch with the electronic device 300. In some implementations, detection thresholds and sensor geometry may be adjusted so that detection of being in close proximity to the body 130 means that the electronic device 300 is very close to the body 130 or almost touching the body 130. In some implementations, close proximity to a body 130 may refer to a distance of less than about 10 mm, less than about 5 mm, less than about 2 mm, or less than about 1 mm between the skin of the body 130 and the electronic device 300. There can be some distance between the sensors 340, 360 and the body 130 to allow for a thickness of the housing 310. Sensitivity and detection thresholds can be adjusted so that once the housing 310 is taken into account, essentially direct physical contact with the electronic device 300 can trigger detection of the electronic device 300. Thus, close proximity to the body 130 can still mean that the electronic device 300 is contacting the body 130 when accounting for device requirements that may separate one or both of the sensors 340, 360 from the body 130 (e.g., thickness of the housing 310).

Figure 3C:
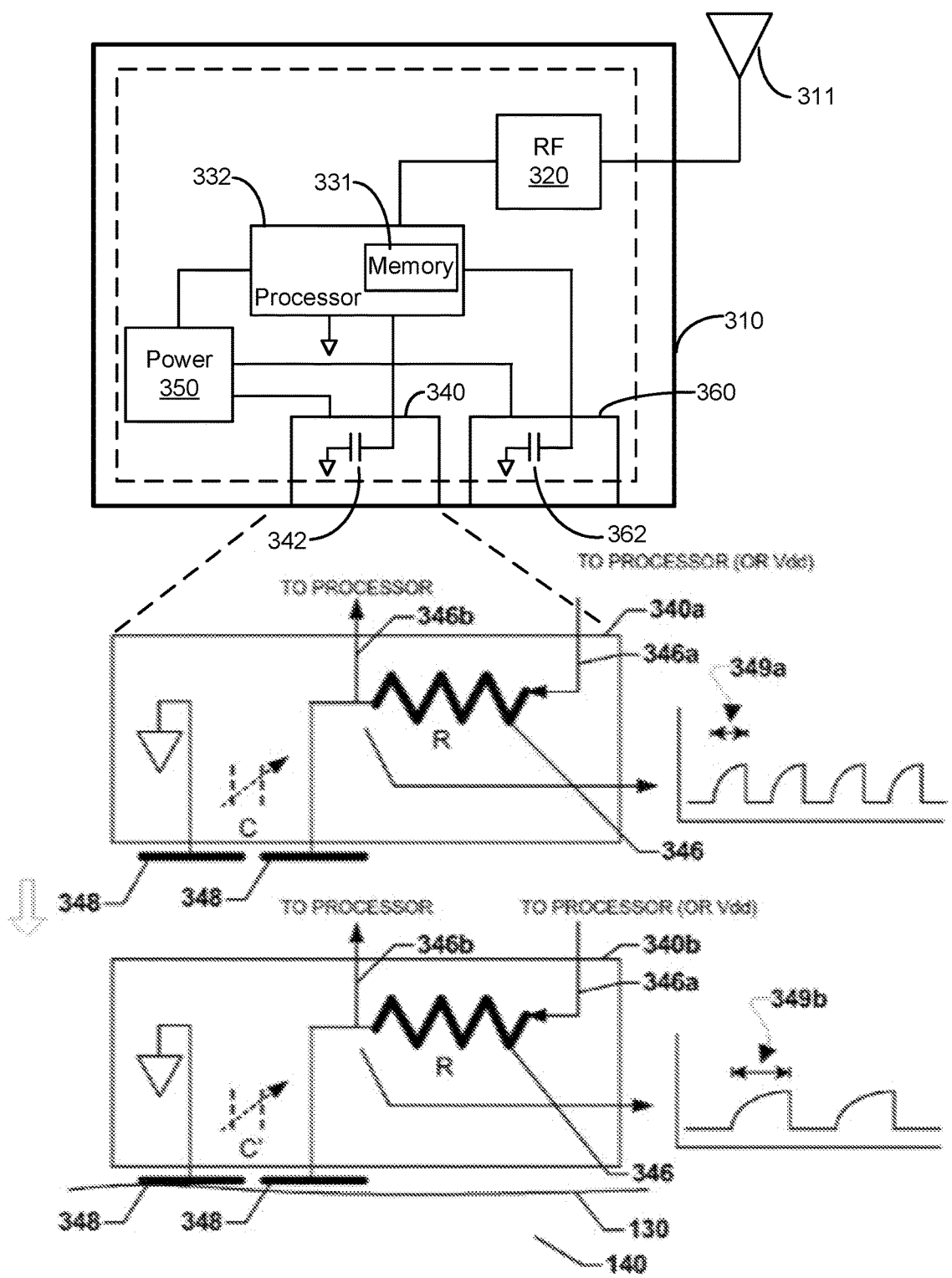
FIG. 3C is a block diagram representation of an example electronic device with a circuit diagram and a timing diagram for a capacitance sensor of the electronic device according to some implementations.
Figure 4A:
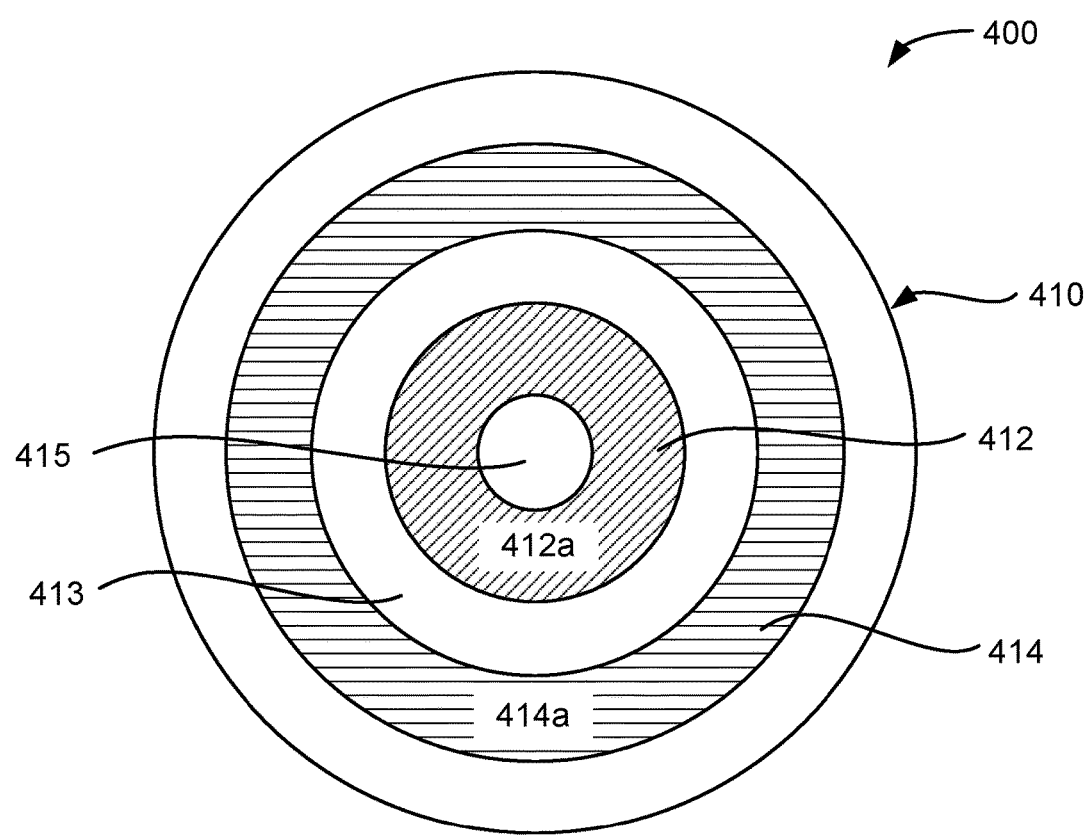
FIG. 4A is a plan view of a schematic representation of an example electronic device including a first active node and a second active node according to some implementations.

FIG. 3C is a block diagram representation of an example electronic device with a circuit diagram and a timing diagram for a capacitance sensor of the electronic device according to some implementations. The capacitance sensor 342 of the first sensor 340 may include one or more conductive surfaces 348. While the one or more conductive surfaces 348 may appear as conductive pads, the conductive surfaces may take on a variety of shapes, sizes, and structures. The different shapes, sizes, and structures of the one or more conductive surfaces 348 may optimize contact of the electronic device 300 over a wide area to increase the likelihood of detection. As shown in FIG. 4A, one or more conductive surfaces 348 may be arranged as concentric rings.

The capacitance sensor 342 may have an effective capacitance C and C', and a resistance R. In FIG. 3C, the one or more conductive surfaces 348 have external surfaces that are not encased within the housing 310. In some implementations, the resistance R is optional, because a current source may drive the capacitance sensor 342. Also, in some implementations, the resistance R and the one or more conductive surfaces 348 may be other components that are functionally equivalent to capacitors and resistors or that provide similar responses to a touch signal applied to the one or more conductive surfaces 348. The illustrated implementations are meant to be illustrative and non-limiting, and show examples of circuits that may be used to achieve a detection operation. Thus, other circuits may be used to detect that the electronic device 300 has been installed, activated, or in use.

In the implementation in FIG. 3C, when the electronic device 300 is not brought in close proximity to or in contact with a body 130, a signal associated with the first sensor 340 may have a given time constant (e.g., RC time constant) based on values of the capacitance C and the resistance R. Such a signal may be generated by stimulating the circuit with a given pulse or signal from either a voltage source or a current source. Such a signal may be applied to node 346a of a resistor 346. A response may be "read" from node 346b, which may be coupled to a pin on the controller 330. For example, a rise time 349a of such a pulse or signal may be measured by the controller 330 by reading the signal on node 346b. Alternatively, the signal may be generated internally in the controller 330 based on the time constant established by values of the capacitance C and the resistance R. Persons skilled in the art will appreciate that other approaches may also be used to take advantage of that relationship established by the values of the capacitance C and the resistance R.

As illustrated in FIG. 3C, when the electronic device 300 is attached to the body 130 and the one or more conductive surfaces 348 are in close proximity to or in contact with the body 130, the effective capacitance of the capacitance sensor 342 changes. This can be due in part to the difference in dielectric properties between air and skin/tissue. In response to the change in capacitance from C to C', the signal associated with the first sensor 340 may have a new time constant (e.g., RC' time constant) based on the new value of the capacitance C' and the resistance R. Such a signal may be generated by energizing or stimulating the first sensor 340 to charge the capacitance sensor 342. Thus, the signal may be generated by stimulating the circuit with a given pulse or signal applied to node 346a and reading the response from node 346b. For example, a rise time 349b of such a pulse or signal may be measured and received by the controller 330. The difference in rise times 349a and 349b may be measured and received by the controller 330, where the difference in rise times 349a and 349b may be indicative of the rate of capacitance charge. As a result, a specified condition of the electronic device 300 may be determined based on the difference in rise times 349a and 349b. While times 349a and 349b are described as rise times, decay times may also be effectively used to calculate the differences in the time constants between detected and non-detected states.

Detected and non-detected states of the electronic device 300 may be determined by comparing readings of the rate of capacitance charge with either previous readings or stored readings that are known to correspond to non-detected states. Depending on the values selected for R and C, for example, the difference between detected and non-detected states may vary greatly. However, some selections for values of R and C may lead to high sensitivity for the electronic device 300. A first sensor 340 with a high sensitivity may be more prone to providing false positive determinations. Values for R and C, in some implementations may further depend on a time used to measure the RC time constant (e.g., rise time, decay time). A further consideration for the values of R and C in some implementations can include the current consumption. Current consumption may depend directly on the applied voltage levels, measurement time, and/or other considerations. In some implementations, in order to provide extended battery life, current consumption may be minimized while preserving detection sensitivity. As noted above, instead of including a resistor 346, similar results may be obtained using a current source to energize the first sensor 340.

Figure 3D:
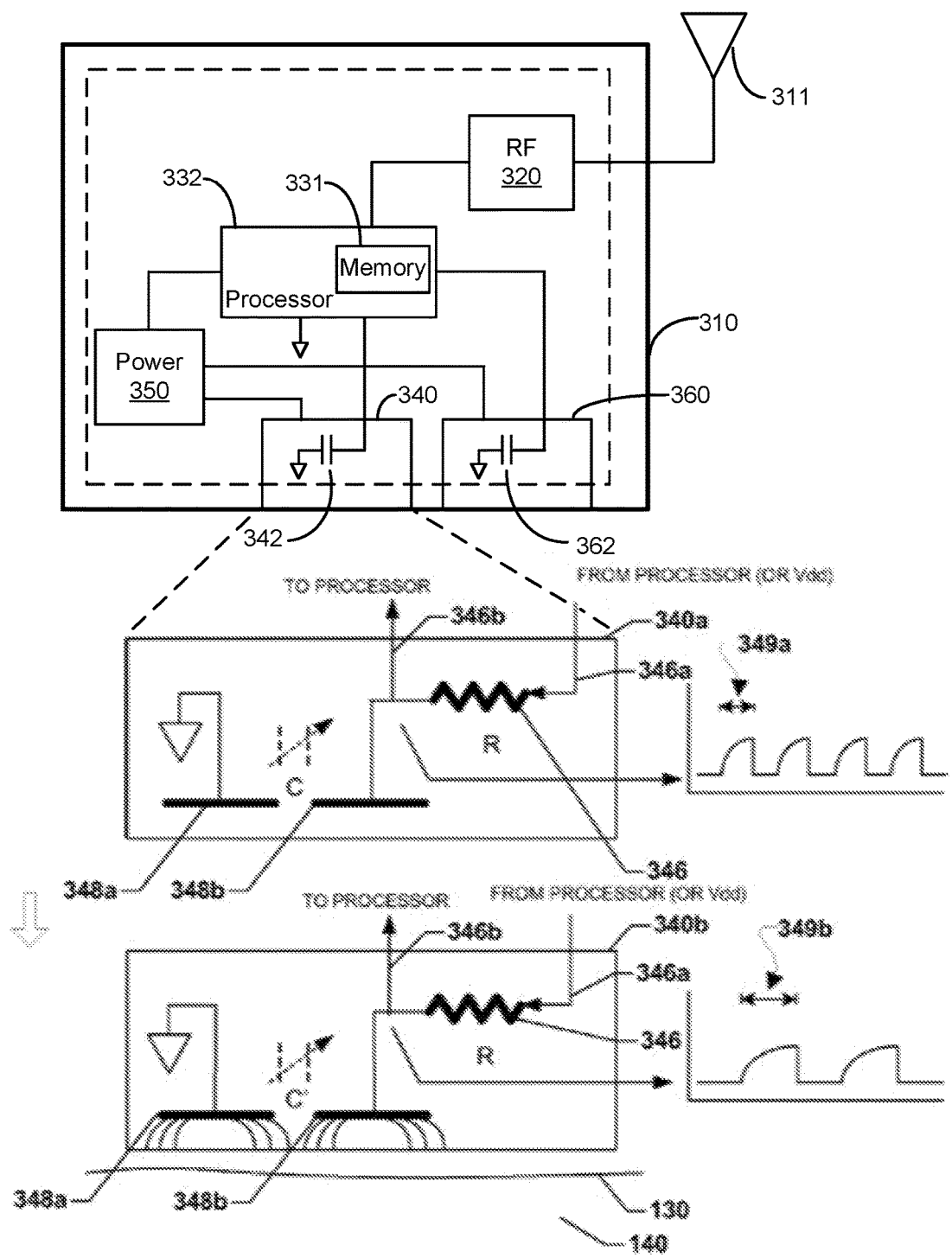
FIG. 3D is a block diagram representation of an example electronic device with a circuit diagram and timing diagram for a capacitance sensor of the electronic device according to some other implementations.

One or both of the first sensor 340 and the second sensor 360 may be configured in a number of ways to enable detecting application/activation of the electronic device 300. FIG. 3D is a block diagram representation of an example electronic device with a circuit diagram and timing diagram for a capacitance sensor of the electronic device according to some other implementations. The first sensor 340 includes one or more active nodes, where each active node has a conductive surface. In FIG. 3D, the first sensor 340 includes a pair of active nodes 348a, 348b. The active nodes 348a, 348b may be encapsulated with other components of the electronic device 300 in housing 310. Because the electronic device 300 may be placed in close proximity to or in contact with a person, exposure to a variety of elements hostile to electronics is possible, such as moisture, water, other fluids or materials, or shock from mechanical contact with devices. Therefore, encapsulation may refer to encasing components of the electronic device 300 in a material, such as a resin or other material, that provides a barrier or seal protecting circuitry from environmental elements. Encapsulation may further provide structural support for delicate components, such as for the purpose of holding the components in a particular placement or orientation, and for protecting the components from damage. In some implementations, the active nodes 348a, 348b may have an effective capacitance between them in detected and non-detected states. When the electronic device 300 comes in close proximity to or in contact with the body 130, the electric fields associated with the active nodes 348a, 348b may be modified, which directly changes the effective capacitance from C to C'. In the present implementation shown in FIG. 3D, the active nodes 348a, 348b may be encapsulated and not in contact with the skin of the body 130. Thus, potential degradation of the active nodes 348a, 348b may be reduced. Encapsulation may further limit the influence of environmental factors, such as moisture, on readings provided by the active nodes 348a, 348b. Further, the encapsulation material may be configured to reduce the potential for irritation of the skin. Thus, by limiting direct contact with the active nodes 348a, 348b and the skin of the body 130, the active nodes 348a, 348b may be protected as well as the skin of the body 130. The difference in the rate of in capacitance charge may be detected by comparing rise times 349a and 349b of a signal that is affected by the change in the RC time constant, from an RC time constant to an RC' time constant.

Figure 3E:
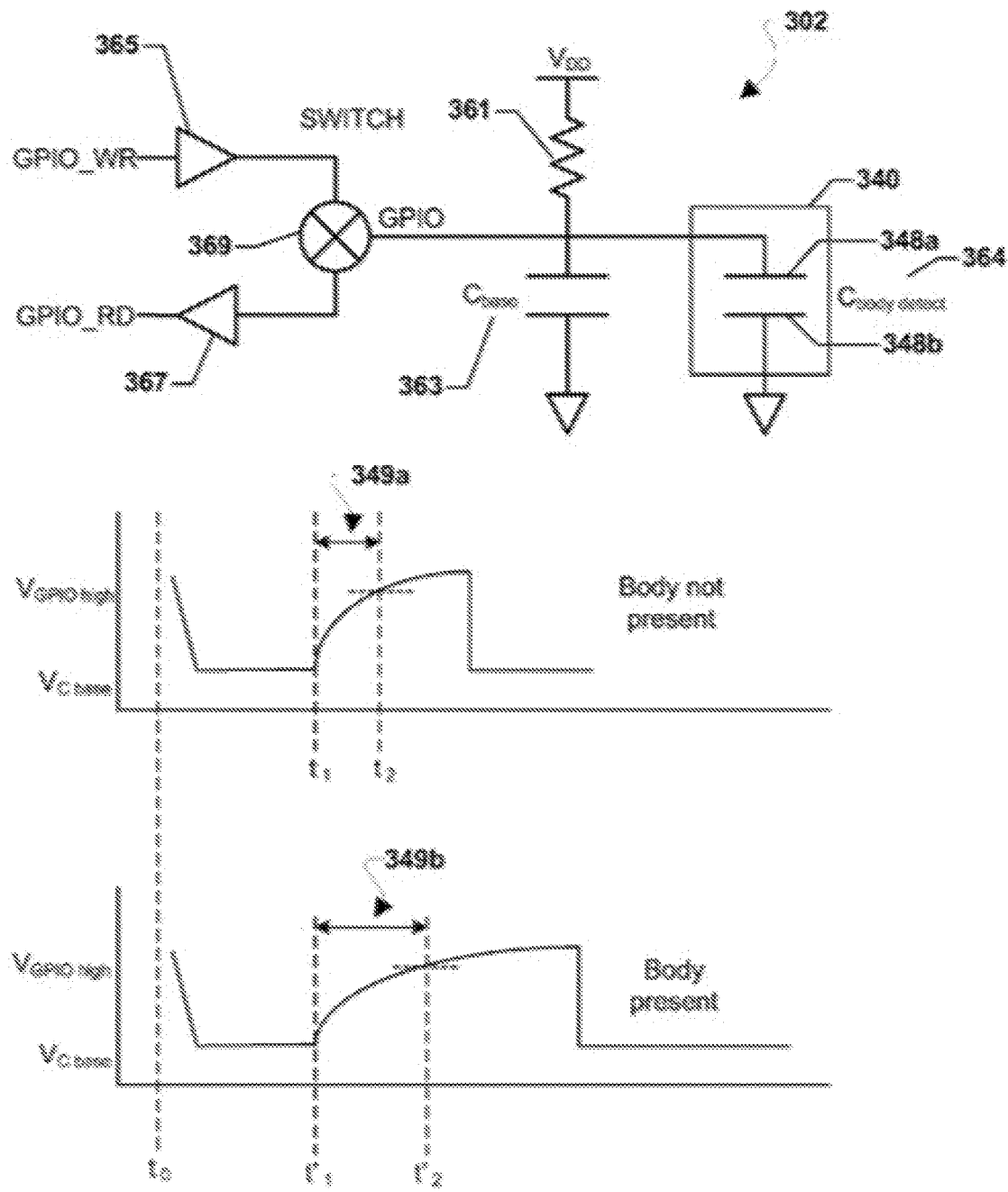
FIG. 3E is a circuit and timing diagram illustrating operation of a capacitance sensor of an example electronic device according to some implementations.

FIG. 3E is a circuit and timing diagram illustrating operation of a capacitance sensor of an example electronic device according to some implementations. In some implementations as shown in implementation 302, a signal may be output or "written" to the first sensor 340 or read from the first sensor 340 from a general purpose input/output (GPIO) pin of the controller 330. The output signal may charge an RC circuit of the first sensor 340, which may be composed of a resistance 361, a base capacitance $C_{base}$ 363, and a body detection capacitance $C_{body\_detect}$ 364. The body detection capacitance $C_{body\_detect}$ 364 may be measured from active nodes 348a, 348b, which in some embodiments can include a pair of conductive surfaces or electrodes. The GPIO pin of the controller 330 may be an input and output pin. The GPIO pin of the controller 330 may be coupled to a switch 369 that switches the GPIO pin between input and output functions.

In an output mode, the switch 369 may be coupled to a pin driver 365. When an output signal GPIO_WR is generated by the controller 330, the output signal may be coupled through the pin driver 365 and the switch 369 to the first sensor 340.

In an input mode, the switch 369 may be coupled to a pin buffer 367 such that an input from the first sensor 340 may be read through the switch 369. Switching the state of the switch 369 may be controlled by the controller 330. For example, the controller 330 may configure the switch 369 in the output mode. The controller 330 may generate the output signal GPIO_WR and apply the signal to the first sensor 340 through the pin driver 365 and the switch 369. The output signal may be applied to the first sensor 340 to energize the first sensor 340 and charge the first sensor 340 at the beginning of a monitoring cycle. The controller 330 may then change the switch 369 to an input mode, where the input signal GPIO_RD may be read through the pin buffer 367, the switch 369, and the first sensor 340. For example, the input signal GPIO_RD may enable the controller 330 to read a charge profile or time constant of the first sensor 340. It is understood that other configurations to apply and read signals from the first sensor 340 are possible.

In some implementations, for example when a body is not present, the controller 330 may switch the operation of the general purpose signal line by applying an output signal GPIO_WR at a time $t_0$. The controller 330 may then switch to an input mode to receive an input signal GPIO_RD from the first sensor 340. The rise characteristic of the signal may be read during a charge phase or the decay characteristic of the signal may be read after the charge phase. In some implementations, at a time $t_1$ a charge period for the combined capacitances of the capacitance $C_{base}$ 363 and the body detection capacitance $C_{body\_detect}$ 364 may begin. The signal may continue to charge until a threshold value is reached, such as at time $t_2$ when a voltage $V_{GPIO\_high}$ is reached. Thus, when the charge/discharge level reaches the threshold value, time $t_2$ may be read and a time 349a between $t_1$ and $t_2$ may be measured.

In some implementations, for example, when a body is present, the controller 330 may switch the operation of the general purpose signal line by applying an output signal GPIO_WR at a time $t_0$. The controller 330 may then switch to an input mode to receive an input signal GPIO_RD from the first sensor 340. Alternatively, a voltage source may be applied to the node 346b as described above, and the controller 330 may manipulate the voltage level on the node 346b by selectively toggling a pin coupled to the resistor 346 to achieve an input signal. The rise or decay characteristic of the signal may be read during a charge or discharge phase, respectively, such as on the node 346b as described herein above. In some implementations when a body is present, at a time $t'_1$ a charge/discharge period for the combined capacitances of the capacitance $C_{base}$ 363 and the body detection capacitance $C_{body\_detect}$ 364 may begin. The presence of the body may change the capacitance of the body detection capacitance $C_{body\_detect}$ 364, having the effect of changing the combined capacitance. The signal may continue to charge or discharge until a threshold value is reached, such as at a time $t'_2$ when a voltage $V_{GPIO\_high}$ is reached. When the charge or discharge level reaches the threshold value, time $t'_2$ may be read and a time 349b between $t'_1$ and $t'_2$ may be measured. In some implementations, the thresholds may be modified to adjust the sensitivity of detecting when a body is present or not.

The difference in the time measurements, such as the difference between the time 349a (e.g., $t_1$ to $t_2$) and the time 349b (e.g., $t'_1$ to $t'_2$), can reflect the different capacitances between a body present and a body not present condition. This difference may thus be used to detect the presence of the body. This difference may be indicative of a rate of capacitance charge of the first sensor 340. Alternatively, the difference between time measurements $t_1$ and $t_2$ and $t'_1$ and $t'_2$ may be used to measure an effective capacitance associated with a body being present or not present. This difference may also be indicative of a rate of capacitance charge of the first sensor 340. Thus, a longer charge cycle for charging the first sensor 340 is generally indicative of the presence of a body. As the capacitance increases due to proximity to a body, the time taken for the first sensor 340 to charge will increase. The presence of the body may indicate that the electronic device 300 is in close proximity to or in contact with the body.

In some implementations, two or more GPIO lines may be used. One GPIO line may be used for applying a signal to charge a capacitance sensor of the first sensor 340, thereby providing a capacitance between active nodes 348a, 348b. The other GPIO line may be used to measure or read the voltage from the capacitance, such as through a direct connection to one or more of the active nodes 348a, 348b.

While the aforementioned description of rise characteristics, decay characteristics, and rate of capacitance charge in FIGS. 3C-3E involve the first sensor 340, the second sensor 360 may include a capacitance sensor 362 capable of performing the same or similar operations as the capacitance sensor 342 of the first sensor 340. Alternatively, the second sensor 360 can be a sensor of a different type, such as an impedance sensor. The second sensor 360 may be useful for providing additional feedback that the electronic device 300 is in close proximity to or in contact with the body 130, thereby providing validation that the electronic device 300 is installed, activated, or in use. Having such an arrangement of sensors 340, 360 may reduce the likelihood of false positives and false negatives. Upon determination that the electronic device 300 is installed, activated, or in use, the electronic device 300 can transition from a low-power mode (e.g., shelf mode) to a high-power mode (e.g., active mode), which allows the electronic device 300 to perform more functions than in the low-power mode. Otherwise, the electronic device 300 may return to the low-power mode to conserve energy.

The electronic device, such as the electronic device 300 as described above, can have a geometry that can improve contact with the skin of a patient's body and increase the likelihood of detecting that the device is in close proximity to or in contact with the body. In some implementations, the geometry of the electronic device can refer to the placement, size, shape, and structure of its active nodes or conductive surfaces. Typically, a capacitance sensor may contact the skin of a patient's body with a metal pad or plate, or two metal pads or plates. One of the metal pads or plates can be connected to a ground node while another one of the metal pads or plates can be connected to an active node. However, in some implementations of the present disclosure, the capacitance sensor can include at least a first active node having a first conductive surface and a second active node having a second conductive surface, where the first conductive surface is separated from the second conductive surface by an electrically insulating layer or surface. Each of the first conductive surface and the second conductive surface may be positioned on a side of the electronic device configured to face/contact a patient's body.

FIG. 4A is a plan view of a schematic representation of an example electronic device including a first active node and a second active node according to some implementations. In some implementations, an electronic device 400 can include the same or similar circuitry, components, and hardware as the electronic device 300 in FIGS. 3A-3E. The electronic device 400 can include a sensor arrangement 410, where the sensor arrangement 410 includes a first active node 412 having a first conductive surface 412a, and a second active node 414 having a second conductive surface 414a. Alternatively, the sensor arrangement 410 can be referred to as including a first sensor 412 having a first conductive surface 412a and a second sensor 414 having a second conductive surface 414a. The first conductive surface 412a and the second conductive surface 414a are separated by an electrically insulating layer or surface 413. The sensor arrangement 410 may refer to one or more sensors of the electronic device 400.

The placement, size, shape, and structure of the sensor arrangement 410 can be arranged to increase contact with the skin of a patient's body. As shown in FIG. 4A, the second conductive surface 414a is positioned in a region near the first conductive surface 412a. The electrically insulating layer 413 separates the second conductive surface 414a from the first conductive surface 412a. The second conductive surface 414a may be positioned on the same surface as the first conductive surface 412a. Accordingly, multiple sensing surfaces positioned on a surface of the electronic device 400 may be employed to detect contact or proximity with the skin of the patient's body. In some implementations, the second conductive surface 414a, the first conductive surface 412a, and the electrically insulating layer 413 are coplanar. A ground node (not shown) may be separated from the first active node 412 and the second active node 414 by one or more electrically insulating layers. An electrically insulating layer 413 may be connected to the ground node.

In some implementations, the surface area of the first conductive surface 412a and the second conductive surface 414a may be optimized for improved contact with skin of a patient's body. As shown in FIG. 4A, the second conductive surface 414a of the second active node 414 includes an area around a perimeter of the first conductive surface 412a of the first active node 412. The second conductive surface 414a and the first conductive surface 412a may each be ring-shaped to form annular layers of electrically conductive material. The second conductive surface 414a is shaped as a concentric ring around a perimeter of the first conductive surface 412a. In some implementations, the second active node 414, the electrically insulating layer 413, and the first active node 412 may form a series of concentric rings around each other, respectively. Such a geometric arrangement can provide an effective gauge of how well the electronic device 400 is adhered to the skin of a patient's body.

In some implementations, the first active node 412 and the second active node 414 may be positioned on an external surface of the electronic device 400 facing the body. In some implementations, the first active node 412 and the second active node 414 may be encapsulated within a housing of the electronic device 400. However, even with encapsulation, changes in the electric fields associated with the nodes of a capacitance sensor can be detected as a result of being in close proximity to or in contact with the skin of a patient's body. Thus, multiple active nodes 412, 414 with multiple conductive surfaces 412a, 414a may be implemented with one or more sensors to determine whether the electronic device 400 is in close proximity to or in contact with the skin of the patient's body.

In some implementations, various parts of an electronic device 400, such as needles of a glucometer or electrodes of an electrocardiograph (EKG), can be used as a sensor to determine or validate if the electronic device 400 is in close proximity to or in contact with a patient's body, or to determine or validate if the electronic device 400 is activated. In fact, such a sensor may be combined with the sensor arrangement 410 to validate the determinations made by the active nodes 412, 414 of the sensor arrangement 410. One or more sensors may be incorporated with such parts of the electronic device 400 (e.g. needle of a glucometer or electrode of an EKG) to provide additional feedback to determine that the electronic device 400 is installed, activated, or in use.

Figure 4B:
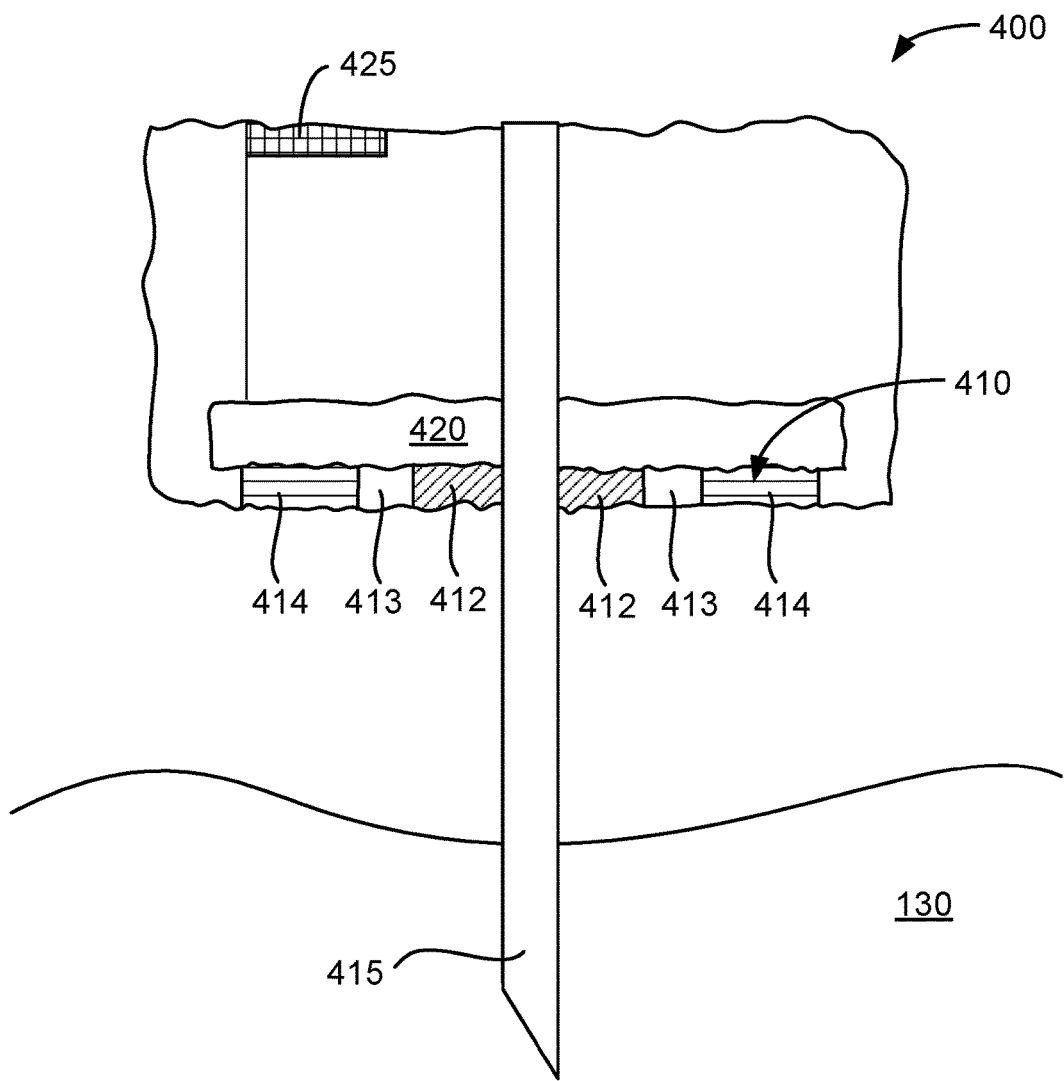
FIG. 4B is a cross-sectional side view of a schematic representation of an example electronic device including multiple sensors according to some implementations.

FIG. 4B is a cross-sectional side view of a schematic representation of an example electronic device including multiple sensors according to some implementations. A sensor arrangement 410 can include a plurality of sensors, where at least one of the sensors in the sensor arrangement 410 includes a capacitance sensor. In FIGS. 4A and 4B, one or more of the sensors in the sensor arrangement 410 can include a first active node 412 having a first conductive surface 412a, and a second active node 414 having a second conductive surface 414a. In some implementations, a first capacitance sensor in the sensor arrangement 410 can include the first active node 412, where the first active node 412 is capable of being stimulated or energized to charge the first capacitance sensor. A second capacitance sensor in the sensor arrangement 410 can include the second active node 414, where the second active node 414 is capable of being stimulated or energized to charge the second capacitance sensor. Alternatively, a capacitance sensor can include the first active node 412 and the second active node 414, where one or both of the nodes 412, 414 are capable of being stimulated or energized to charge the capacitance sensor. At least one of the first capacitance sensor including the first active node 412, the second capacitance sensor including the second active node 414, and the capacitance sensor including the first active node 412 and the second active node 414 may be referred to as a "first sensor."

As shown in FIGS. 4A and 4B, the electronic device 400 can include one or more needles 415. The one or more needles 415 are capable of piercing through skin of the body 130. At least one of the needles 415 is configured to extend through a housing of the electronic device 400 and out of the side of the electronic device 400 facing/contacting the body 130. The at least one needle 415 may extend through a portion of the electronic device 400 surrounded by the first conductive surface 412a of the first active node 412. The one or more needles 415 can include an additional sensor in the sensor arrangement 410. In some implementations, the additional sensor can be a capacitance sensor, an impedance sensor, ohmic sensor, or a mechanical switch. The additional sensor may be used in conjunction with components/sensors for taking readings of the body 130, such as a needle of a glucometer or electrodes of an EKG. This additional sensor may be referred to as a "second sensor."

With a capacitance sensor as part of the one or more needles 415, the one or more needles 415 may be capable of determining that the electronic device 400 is in close proximity to or in contact with the body 130 because the capacitance in the capacitance sensor will change when approaching skin or tissue because of the different dielectric properties compared to air. In some implementations, the one or more needles are capable of being stimulated or energized to charge the capacitance sensor. A signal can be generated by the capacitance sensor that is indicative of the rate of capacitance charge of the capacitance sensor. If the rate of capacitance charge is greater than a threshold value (e.g., longer charge cycle time), then it can be determined that the electronic device 400 is in close proximity to or in contact with the body 130.

When at least one of the needles 415 pierces through the skin of a patient's body 130, an active node and a ground node of a capacitance sensor can be defined with respect to the patient's limb/body. The one or more needles 415 may form a capacitance sensor with the body 130, or the one or more needles 415 may form a capacitance sensor with one or both of the conductive surfaces 412a, 414a.

In some implementations, a top portion of a needle 415 may expose a ground layer to define a ground node, and a bottom portion (i.e., towards the tip) of the needle 415 may expose an active node in the patient's body 130. This can occur, for example, when the bottom portion of the needle 415 contacts conductive fluid inside the patient's body 130. A capacitive effect would be created to the conductive fluid, where contact with the conductive fluid inside the patient's body 130 increases the capacitance. When the needle 415 is stimulated or energized at the active node, the rate of capacitance charge can be measured.

In some implementations, a bottom portion (i.e., towards the tip) or other portion of the needle 415 may form a ground node inside the patient's body 130. An active node may be in close proximity to or in contact with the skin of the patient's body 130. For example, one or both of the conductive surfaces 412a, 414a may be in close proximity to or in contact with the skin of the patient's body 130. A capacitive effect would be created to one or both of the conductive surfaces 412a, 414a, where contact with the skin of the patient's body 130 increases the capacitance. When the needle 415 is stimulated or energized at the active node, the rate of capacitance charge can be measured.

With an impedance sensor as part of the one or more needles 415, the one or more needles 415 may be capable of determining that the electronic device 400 is in contact with the skin of the patient's body 130. The one or more needles 415 may use ohmic sensing to determine contact with the skin of the patient's body 130. A needle 415 inserted into skin or tissue of a patient's body 130 can establish an electrically conductive pathway through the patient's body 130. When the needle 415 is not in contact with the skin or tissue of the patient's body 130, then the electrical impedance between the needle 415 and a housing of the electronic device 400 can be very high. When the needle 415 is in contact with the skin or tissue of the patient's body 130, then the electrical impedance between the needle 415 and the housing of the electronic device 400 drops. This change in electrical impedance can be measured to detect whether the electronic device 400 is in contact with the patient's body 130, and can provide additional feedback that the electronic device 400 is installed, activated, or in use.

In some implementations, at least one of the needles 415 is part of an electronic device which is a glucometer. Thus, the one or more needles 415 can further include a subcutaneous glucose sensor (not shown). The subcutaneous glucose sensor is capable of piercing the skin of the body 130 and measuring a concentration of glucose in the body 130. Where the second sensor (e.g., capacitance sensor, impedance sensor, etc.) is part of the one or more needles 415, the second sensor is separate from the subcutaneous glucose sensor. That way, the second sensor does not interfere with the function of measuring glucose concentration in the glucometer. However, it will be understood that the subcutaneous glucose sensor can provide readings that can be used to validate that the electronic device 400 is installed, activated, or in use. Thus, the subcutaneous glucose sensor may also be referred to as a "second sensor" or "third sensor."

In some implementations, the electronic device 400 includes a plurality of electrodes (not shown) capable of contacting skin of the body 130 and recording electrical activity of the body 130. One or more of the electrode pads may be used as part of a sensor, such as a capacitance sensor, for determining if the electronic device 400 is in close proximity to or in contact with the body 130. In some implementations, at least one of the plurality of electrodes can serve as an active node and at least one of the plurality of electrodes can serve as a ground electrode. In some implementations, a direct measurement of impedance between two or more electrodes can determine if the electronic device is in close proximity to or in contact with the body 130. The plurality of electrodes may be part of an EKG.

As shown in FIG. 4B, the electronic device 400 can further include a sensor 425. The sensor 425 may be one of the plurality of sensors in the sensor arrangement 410. The sensor 425 may reinforce and further validate determinations made by sensor readings from the conductive surfaces 412a, 414a and/or the needle 415. In some implementations, the sensor 425 is positioned on a side of the electronic device 400 configured to face away from the body 130. The sensor 425 may be positioned on an external surface of the housing or the base of the electronic device 400, or within the housing or the base of the electronic device 400. In some implementations, the sensor 425 is coupled to an antenna. The sensor 425 may also be referred to as a "third sensor" or as a "fourth sensor."

In some implementations, the sensor 425 is a capacitive touch sensor. The capacitive touch sensor may provide feedback to the electronic device 400 that the electronic device 400 has been installed, activated, or in use. For example, a finger or other object can press the capacitive touch sensor as further validation that the electronic device 400 is in close proximity to or in contact with the patient's body 130. The capacitive touch sensor may be pressed for a sufficiently long duration and with sufficient force to make such a determination or validation. This can reduce the likelihood of routine handling and/or inadvertent pressing of the capacitive touch sensor for false positive determinations.

In some implementations, the sensor 425 includes an electrode disposed on a base of the electronic device 400. The base of the electronic device 400, such as a base 120 described in FIG. 1, may be detachable. For example, the electrode may be incorporated on a tear-off backing of the electronic device 400. Where the electronic device 400 is a packaged product, the sensor 425 may be added to the electronic device 400 for ease of assembly. That way, no internal changes occur with respect to the packaging of the packaged product.

When the base of the electronic device 400 is removed, the electrode is separated from the rest of the electronic device 400. In some implementations, the sensor 425 is a capacitance sensor where the increased distance between the electrode disposed on the detached base and the rest of the electronic device 400 will decrease the capacitance of the capacitance sensor. An antenna coupled with the sensor 425 can communicate to the electronic device 400 that the base has been removed, thereby indicating that the electronic device 400 has been opened, unpacked, unsealed, etc. In some implementations, the antenna can communicate over a Bluetooth frequency band or other wireless communications protocol to a controller of the electronic device 400. The antenna can also communicate with a remote device, such as a smartphone, to provide feedback regarding the sequence of activation of the electronic device 400.

The electronic device 400 may further include a circuit board 420. Each of the plurality of sensors in the sensor arrangement 410 may be coupled to the circuit board 420. The circuit board 420 may include a variety of electrical components, including electrical components described in FIGS. 3A-3E. In some implementations, the circuit board 420 includes a controller (not shown). In some implementations, the circuit board 420 may be a rigid or semi-rigid circuit board. Alternatively, the circuit board 420 may be a flexible circuit board.

Each of the first, second, and third sensors in the sensor arrangement 410 may be coupled to the controller of the circuit board 420. The controller may be configured to stimulate or energize the first sensor and receive a first measurement from the first sensor. In some implementations, the first measurement may be indicative of a rate of capacitance charge of a capacitance sensor. The controller may be configured to determine that the electronic device 400 is in close proximity to or in contact with the body 130, such as when the first measurement is greater than a first threshold value. The controller may also be configured to stimulate or energize the second sensor and receive a second measurement from the second sensor in response to determining that the electronic device 400 is in close proximity to or in contact with the body 130. In some implementations, the second measurement may be indicative of a rate of capacitance charge of a capacitance sensor. The controller may be configured to determine that the electronic device 400 is activated based on one or both of the first measurement and the second measurement, such as when the second measurement is greater than a second threshold value. The controller may also be configured to receive a third measurement from the third sensor in response to determining that the electronic device 400 is activated. In some implementations, the third measurement may be indicative of the third sensor being touched for a sufficient duration or indicative of a base being detached from a housing. The controller may be configured to validate that the electronic device 400 has been activated based on the first measurement, the second measurement, the third measurement, or any combination thereof.

Figure 5:
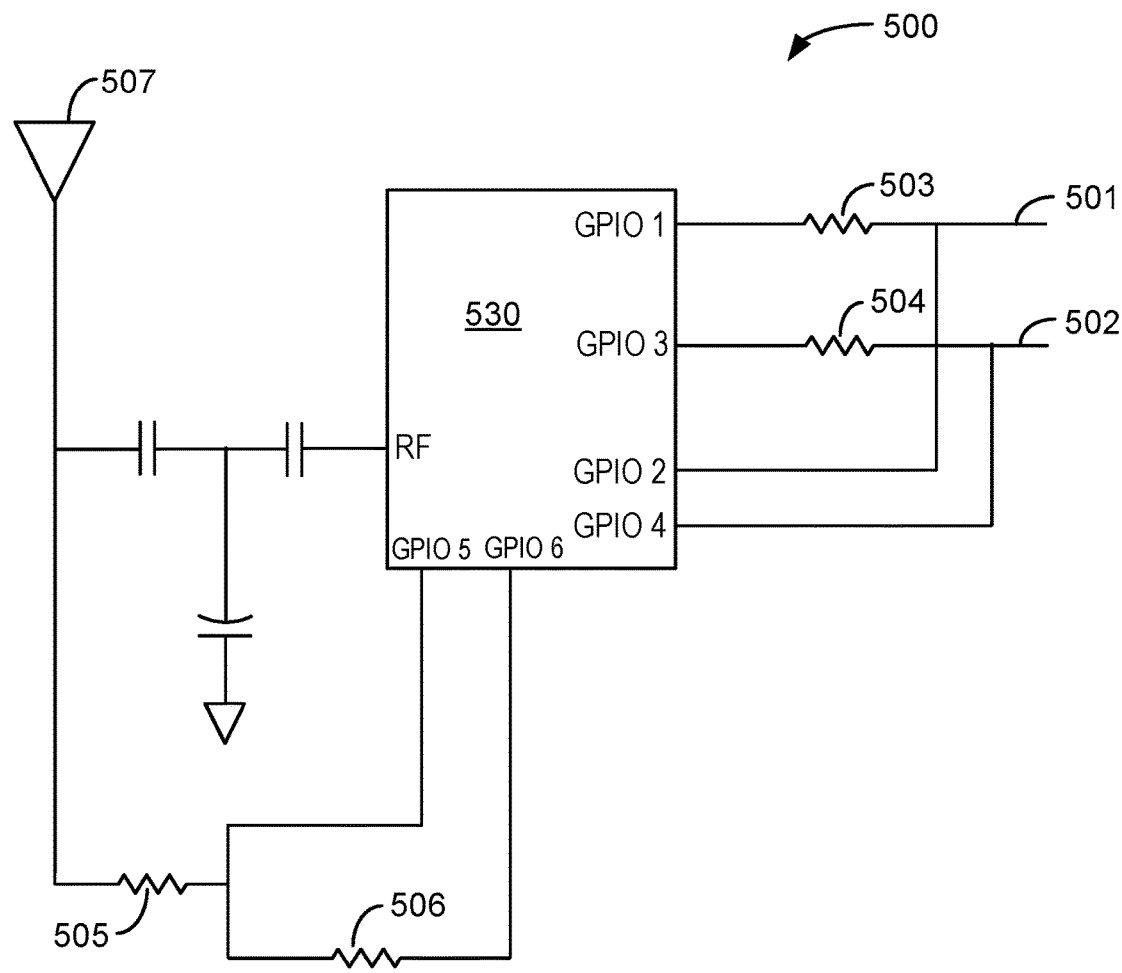
FIG. 5 is a circuit diagram representation of an example electronic device including a first sensor, a second sensor, and a third sensor according to some implementations.

FIG. 5 is a circuit diagram representation of an example electronic device including a first sensor, a second sensor, and a third sensor according to some implementations. Multiple sensors may be used in a circuit assembly to detect and validate whether an electronic device 500 is in close proximity to or in contact with a body, which can ultimately determine and validate whether the electronic device 500 has been installed, activated, or in use. Multiple sensors increase the likelihood of detection, and multiple sensors can be implemented to provide multiple stages for activating the electronic device as discussed below.

As shown in FIG. 5, an electronic device 500 includes a first sensor 501, a second sensor 502, and a third sensor 507. In some implementations, at least one of the first sensor 501 and the second sensor 502 is part of a needle or an electrode of an EKG. In some implementations, a first active node of a first capacitance sensor can represent the first sensor 501 in the circuit diagram, and a second active node of a second capacitance sensor can represent the second sensor 502 in the circuit diagram.

The first active node 501 can be coupled to a first resistor 503, and the first resistor 503 can be coupled to a controller 530 via a GPIO line1. The first active node 501 can be coupled directly to the controller 530 via a GPIO line2. In order to measure a capacitance of the first capacitance sensor, GPIO line1 would apply a voltage or current through the first resistor 503 and charge the first capacitance sensor at the first active node 501, and GPIO line2 directly connected to the first active node 501 would read or measure the voltage or current from the capacitance coming from the first capacitance sensor. Similarly, the second active node 502 can be coupled to a second resistor 504, and the second resistor 504 can be coupled to the controller 530 via a GPIO line3. The second active node 502 can be coupled directly to the controller 530 via a GPIO line4. In order to measure a capacitance of the second capacitance sensor, GPIO line3 would apply a voltage or current through the second resistor 504 and charge the second capacitance sensor at the second active node 502, and GPIO line4 directly connected to the second active node 502 would read or measure the voltage or current from the capacitance coming from the second capacitance sensor.

In some implementations, a third sensor 507 can be coupled to an antenna of the electronic device 500. The antenna can be coupled to a third resistor 505, which is coupled to the controller 530 via a GPIO line5. The antenna may be coupled to a fourth resistor 506, and the fourth resistor 506 can be coupled to the controller 530 via a GPIO line6. In some implementations, the third resistor 505 can be relatively small compared to the fourth resistor 506. Where the third sensor 507 is a third capacitance sensor, the GPIO line6 may apply a voltage or current through the fourth resistor 506 to charge the third capacitance sensor, and the GPIO line5 would read or measure the voltage or current coming from the third capacitance sensor. In some implementations, the third sensor 507 is a capacitive touch sensor.

Each of the first sensor 501, the second sensor 502, and the third sensor 507 may be implemented in an activation or validation sequence for the electronic device 500. For example, a remote device (e.g., smartphone) can provide step-by-step instructions to guide the activation of the electronic device 500 as it ascertains the status of each of the sensors 501, 502, and 507. For example, the first sensor 501 can be a capacitance sensor that detects removal of an adhesive base or detects placement of the electronic device 500 on the skin of a patient's body. The electronic device 500 can transition from a low-power mode to a high-power mode, and connect to the remote device. The remote device can guide a user through the remainder of the activation or validation sequence. In some implementations, the second sensor 502 can be a capacitance sensor or ohmic sensor that is part of a needle of a glucometer. The remote device can provide further instructions for activating or validating the electronic device 500 using the needle, where the needle can be injected and subsequently withdrawn. The second sensor 502 can detect that the electronic device 500 is properly used. In some implementations, the third sensor 507 can be a capacitive touch sensor or even actual probes of the glucometer. The third sensor 507 can provide additional feedback to the remote device that the electronic device 500 is properly used. Each step in the activation or validation sequence can be monitored by the remote device and provide immediate feedback to the user. That way, if something goes wrong, the user can try again. The process flow in the flow diagrams in FIG. 6 and FIG. 7 may illustrate some example activation and validation sequences. However, it will be understood that other activation and validation sequences may be possible with multiple sensors of an electronic device.

Figure 6:
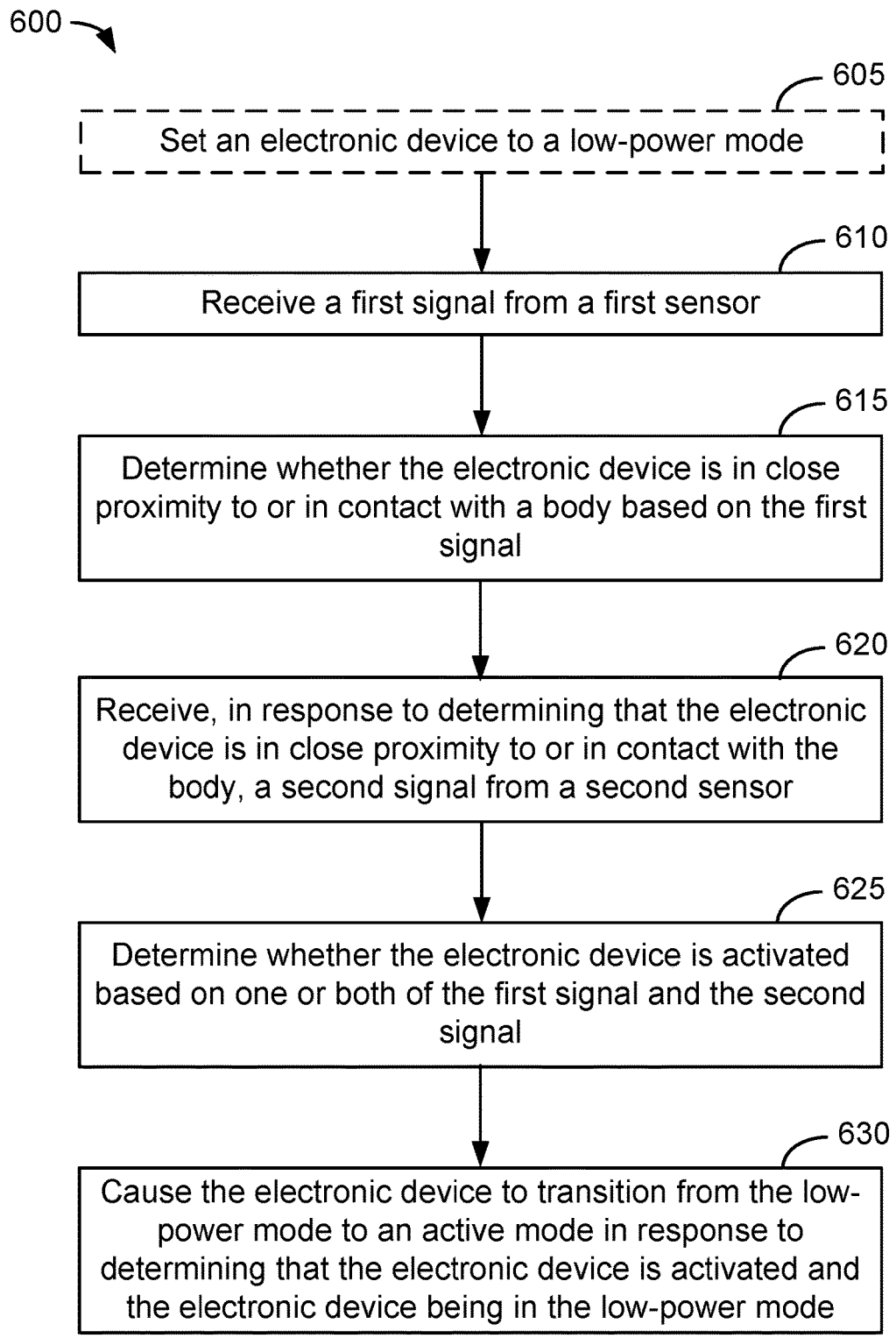
FIG. 6 is a flow diagram illustrating an example method of an electronic device in a low-power mode for determining whether the electronic device is activated according to some implementations.

FIG. 6 is a flow diagram illustrating an example method of an electronic device in a low-power mode for determining whether the electronic device is activated according to some implementations. The process 600 may be performed in a different order or with different, fewer, or additional operations. In some implementations, the process 600 may be performed by the electronic device 100 in FIG. 1, the electronic device 200 in FIG. 2, the electronic device 300 in FIGS. 3A-3E, the electronic device 400 in FIGS. 4A and 4B, or the electronic device 500 in FIG. 5. In some implementations, the blocks of the process 600 may be implemented, at least in part, according to software stored on one or more non-transitory computer readable media.

The process 600 relates at least in part to a process of detecting whether an electronic device is in close proximity to or in contact with a body. Such detection can be indicative of whether the electronic device being applied to the body is properly installed, activated, or in use. In some implementations, the process 600 relates at least in part to a process of determining whether the electronic device is activated and validating that determination.

At block 605 of the process 600, an electronic device is set to a low-power mode. The block 605 is optional in the process 600, as the process 600 for determining whether the electronic device is activated may begin with the electronic device already in a low-power mode. An electronic device can operate in different modes or power states to manage consumption of power. In some implementations, the process 600 can further include setting the electronic device to a manufacturing mode prior to setting the electronic device to a low-power mode. During the manufacturing mode, all or almost all the electronic components of the electronic device are turned off. However, a low-power clock may run continuously during the manufacturing mode. The process 600 can further include determining that a duration of time has elapsed in the manufacturing mode, where the electronic device transitions from the manufacturing mode to the low-power mode after the duration of time has elapsed.

In some implementations, the low-power mode can refer to the shelf mode as described above. In some implementations, one or more peripheral electronic components in the electronic device are disabled in the low-power mode. This can include, for example, a wireless communications component and one or more sensors for measuring detectable physical quantities (e.g., temperature, pulse rate, blood pressure, blood glucose levels, etc.). Thus, not all the available functions of the electronic device are enabled in the low-power mode. However, a low-power clock may continuously run in a low-power mode, where the low-power clock may enable one or more sensors for detecting specified conditions of the electronic device to periodically wake up. The one or more sensors for detecting specified conditions of the electronic device may be woken up in regular time intervals. In some implementations, after a regular time interval, a high-power clock may turn on to generate a full duty clock signal for a sufficiently short period of time to detect if the specified conditions are met. During the sufficiently short period of time, a voltage or current can be applied to a first sensor to charge the first sensor, where the first sensor includes a first capacitance sensor. In other words, after a predetermined time interval and for a short duration, the first sensor can be energized to charge the first capacitance sensor. After charging first capacitance sensor for the short duration, the first sensor may generate a signal to be received by a controller.

At block 610 of the process 600, a first signal is received from the first sensor. The first signal may be received by a controller of the electronic device. The first signal may be generated after stimulating or energizing an active node of the first capacitance sensor. The first signal may include rise characteristics or decay characteristics of the first capacitance sensor. The first signal may include a measurement of the capacitance of the first capacitance sensor and may be indicative of a rate of capacitance charge of the first capacitance sensor. In some implementations, the process 600 can further include measuring the rate of capacitance charge of the first capacitance sensor. The rate of capacitance charge can represent the rate at which a capacitor charges until a certain voltage is reached when the capacitor in the first capacitance sensor is charged. In some implementations, the rate of capacitance charge of the first capacitance sensor during the short duration that the first sensor is charged can be compared against a threshold value.

At block 615 of the process 600, whether the electronic device is in close proximity to or in contact with a body based on the first signal is determined. For example, if the first signal is greater than the threshold value, then the electronic device is determined to be in close proximity to or in contact with the body. In some implementations, a controller may process the first signal by measuring rise times or decay times, and calculating a difference in time constants between states (e.g., detected and non-detected states). If the calculated difference associated with the first signal is greater than the threshold value, then the electronic device is determined to be in close proximity to or in contact with the body. Generally, the rate of capacitance charge increases with closer proximity to the skin of the body.

In some implementations, the electronic device is determined to not be in close proximity to or in contact with the body based on the first signal. In such instances, the first sensor would return to sleep, and the electronic device may continue to operate in a low-power mode. A low-power clock would wake up the first sensor would to perform another detection operation after the predetermined time interval.

In contrast to a typical capacitive touch sensor, the first sensor includes a capacitance sensor that is charged for a short period of time and a rate of capacitance charge is measured. In other words, the capacitance sensor of the first sensor is pulsed very briefly, a calculation is quickly performed to generate a measurement of the rate in which the capacitance sensor charges. This may significantly reduce the power consumed in detecting whether an electronic device is in close proximity to or in contact with a body. In contrast, for example, a typical capacitive sensor may employ an oscillator that goes through multiple cycles to produce an oscillator frequency associated with the capacitance of the capacitive touch sensor. Not only does this take longer (e.g., on the order of a few milliseconds), this utilizes more processing power than the capacitance sensor of the present disclosure.

At block 620 of the process 600, a second signal is received from a second sensor in response to determining that the electronic device is in close proximity to or in contact with the body. In some implementations, the second signal may be indicative of a measurement of a capacitance of a second capacitance sensor. In some implementations, the process 600 can further include measuring the rate of capacitance charge of the second capacitance sensor. The second signal may be generated after stimulating or energizing an active node of the second capacitance sensor, thereby charging the second capacitance sensor. In some implementations, a rate of capacitance charge of the second capacitance sensor during the short duration that the second capacitance sensor is charged can be compared against a threshold value. In one example, the second signal may be received from the second capacitance sensor of one or more needles, such as one or more needles of a glucometer. In one example, the second signal may be received from the second capacitance sensor of conductive surfaces positioned on a side of the electronic device configured to face/contact the body. In one example, the second signal may be received from the second capacitance sensor of a touch sensor or antenna positioned on a side of the electronic device configured to face away from the body. The second signal may be received by a controller of the device.

At block 625 of the process 600, the electronic device is determined to be activated based on one or both of the first signal and the second signal. For example, if the second signal is greater than the threshold value, then the electronic device is determined to be activated or further determined to be in close proximity to or in contact with the body. In some implementations, a controller may process the second signal by measuring rise times or decay times, and calculating a difference in time constants between states (e.g., detected and non-detected states). If the calculated difference associated with the second signal is greater than the threshold value, then the electronic device is further determined to be installed, activated, or in use.

An electronic device with a first capacitance sensor may be prone to providing false positive determinations if detection is only limited to the first capacitance sensor. Additionally, the electronic device with only a capacitive touch sensor may be prone to providing false positive determinations if detection is only limited to the capacitive touch sensor.

At block 630 of the process 600, the electronic device is caused to transition from the low-power mode to an active mode in response to determining that the electronic device is activated and the electronic device being in the low-power mode. Determination that the electronic device is activated can be made according to an activation or validation sequence. In the active mode, the electronic device is fully operational and all the sensors and the peripheral electronic components are activated. The wireless communications component may be activated during the active mode. One or more sensors for taking readings and/or measurements of the body may be activated during the active mode. The high-power clock and the low-power clock may operate continuously or as may be called for under the control of the controller. Thus, the full operations of the electronic device are available during the active mode.

The electronic device is determined to be activated based at least in part on the first signal and the second signal in order to transition from a low-power mode to an active mode. If only the first signal is above a first threshold value but the second signal is not above a second threshold value, or if only the second signal is above the second threshold value but the first signal is not above the first threshold value, then the electronic device is determined to not be activated. Moreover, if neither the first signal nor the second signal is above the first threshold value and the second threshold value, respectively, then the electronic device is determined to not be in close proximity to the body.

In some implementations, the process 600 further includes detecting the electronic device being no longer in close proximity to the body. In such instances, the electronic device may return to the low-power mode, thereby disabling peripheral electronic components and the wireless communications component and periodically waking up the first sensor and the second sensor to perform detection operations. The electronic device remains in the low-power mode to conserve battery life. Furthermore, the detection operations performed by the first sensor and the second sensor provide a relatively short sensing interval for improved responsiveness and reduced power consumption. The electronic device remains in the low-power mode until specified conditions are met, namely that the electronic device is determined to be in close proximity to or in contact with a body and determined to be installed, activated, or in use.

Figure 7:
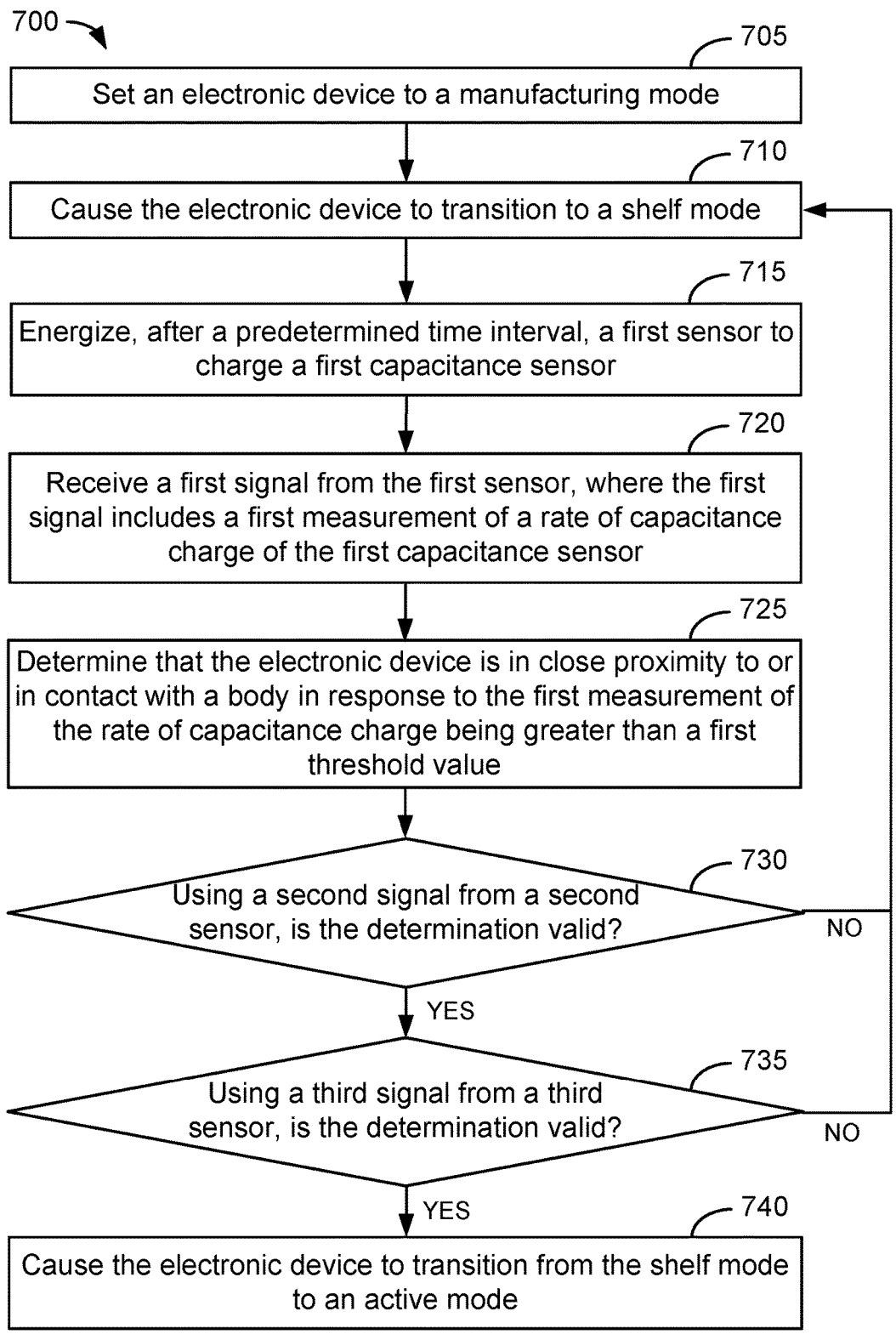
FIG. 7 is a flow diagram illustrating an example method for detecting and validating activation of an electronic device according to some implementations.

FIG. 7 is a flow diagram illustrating an example method for detecting and validating activation of an electronic device according to some implementations. At least some operations of the process 700 provide a validation sequence before transitioning the electronic device from a low-power mode to an active mode. The process 700 may be performed in a different order or with different, fewer, or additional operations. In some implementations, the process 700 may be performed by the electronic device 100 in FIG. 1, the electronic device 200 in FIG. 2, the electronic device 300 in FIGS. 3A-3E, the electronic device 400 in FIGS. 4A and 4B, or the electronic device 500 in FIG. 5. In some implementations, the blocks of the process 700 may be implemented, at least in part, according to software stored on one or more non-transitory computer readable media.

At block 705 of the process 700, an electronic device is set to a manufacturing mode. In a manufacturing mode or factory mode, the electronic device can be in its lowest-power mode. Peripheral electronic components, high-power clock, wireless communications components, sensors for performing detection operations of the electronic device, and sensors for taking readings or measurements of the body may be disabled during the manufacturing mode. However, a controller may begin and continue operation of a low-power clock. The low-power clock can allow the controller to know the elapsed time since activation (e.g., battery installation) and track a remaining time for the manufacturing mode.

At block 710 of the process 700, the electronic device is caused to transition to a shelf mode. In a shelf mode or detection mode, the electronic device can be in a low-power mode that consumes more power than the manufacturing mode or factory mode. After the low-power clock in the manufacturing mode determines that predetermined duration of time has elapsed, the electronic device can transition to the shelf mode. In the shelf mode, the low-power clock can use a timer to track when a predetermined time interval has elapsed. In addition, sensors for performing detection operations of the electronic device are periodically enabled during the shelf mode. The high-power clock may be periodically enabled for a brief period of time to complete detection operations. However, the peripheral electronic components, the wireless communications device, the sensors for taking readings or measurements of the body, or any combination thereof may remain disabled during the shelf mode.

At block 715 of the process 700, a first sensor is energized after a predetermined time interval to charge a first capacitance sensor. Energizing the first sensor may involve applying a voltage from a voltage source or a current from a current source to an active node. In some implementations, the active node of the first capacitance sensor can have one or more conductive surfaces configured for different placements, sizes, shapes, and structures to optimize contact with a body. For example, multiple conductive surfaces may be positioned on the same surface on a side of the electronic device configured to face/contact the body. The conductive surfaces may be separated by one or more electrically insulating layers. The first capacitance sensor can have a ground node separated from the active node by an electrically insulating layer. The ground node and the active node are electrically conductive. The geometry of the first sensor can be adjusted to influence the sensitivity of the detection of the electronic device. In some implementations, the geometry of the first sensor can be similar to the geometry of the sensor arrangement in FIG. 4A. In some implementations, the first capacitance sensor may be part of a needle, where the needle or a portion of the needle is energized or stimulated. Where the first capacitance sensor is part of the needle, the active node or the ground node of the first capacitance sensor may be inside a body.

At block 720 of the process 700, a first signal from the first sensor is received, where the first signal includes a first measurement of a rate of capacitance charge of the first capacitance sensor. The first signal may be generated after stimulating or energizing an active node of the first capacitance sensor. The first signal may include rise characteristics or decay characteristics of the first capacitance sensor. The first signal may include a measurement of the capacitance of the first capacitance sensor and may be indicative of a rate of capacitance charge of the first capacitance sensor. In some implementations, the process 700 can further include measuring a first capacitance charge rate of the first capacitance sensor. The capacitance charge rate can represent the rate at which a capacitor charges until a certain voltage is reached when the capacitor in the first capacitance sensor is charged. In some implementations, the capacitance charge rate of the first capacitance sensor during the short duration that the first capacitance sensor is charged can be compared against a first threshold value. The first signal may be received by a controller of the electronic device.

At block 725 of the process 700, the electronic device is determined to be in close proximity to or in contact with a body in response to the first capacitance charge rate being greater than a first threshold value. The controller of the electronic device can measure and compare the first capacitance charge rate against the first threshold value. Such a determination can initiate a feedback sequence to not only validate that the electronic device is in close proximity to or in contact with the body, but to also determine that the electronic device is installed, activated, or in use. In some implementations, the determination at block 725 can be communicated via a wireless communications component to a remote device. The remote device may provide feedback for instructing a user to proceed to additional operations for validating detection and validating activation.

If it is determined that the electronic device is in close proximity or in contact with the body, the process 700 continues to block 730. At block 730 of the process 700, the determination made at block 725 is validated using a second signal from a second sensor. The second sensor can serve as reinforcement that the electronic device is actually in close proximity to or in contact with the body, and/or determine that a component of the electronic device is being properly used or installed. Advancement of the use or installation of the electronic device can be stalled if the remote device determines from the second sensor that the component of the electronic device is not properly used or installed. In some implementations, the second sensor is a second capacitance sensor. The second capacitance sensor can be coupled to the same sensor arrangement as the first capacitance sensor, or the second capacitance sensor can operate independently from the first capacitance sensor. In some implementations, an active node (different than the active node of the first capacitance sensor) of the second capacitance sensor can have one or more conductive surfaces configured for different placements, sizes, shapes, and structures to optimize contact with the body. For example, multiple conductive surfaces may be positioned on the same surface on a side of the electronic device configured to face/contact the body. The conductive surfaces may be separated by one or more electrically insulating layers or surfaces. The second capacitance sensor can have a ground node separated from the active node by an electrically insulating layer. The ground node and the active node are electrically conductive. In some implementations, the second capacitance sensor may be part of a needle, where the needle or a portion of the needle is energized or stimulated. Where the second capacitance sensor is part of the needle, the active node or the ground node of the second capacitance sensor may be inside the body.

A second signal from the second sensor is received, where the second signal includes a measurement of a rate of capacitance charge of the second capacitance sensor. The second signal may be generated after stimulating or energizing an active node of the second capacitance sensor. The second signal may include rise characteristics or decay characteristics of the second capacitance sensor. The second signal may include a measurement of the capacitance of the second capacitance sensor and may be indicative of a rate of capacitance charge of the second capacitance sensor. In some implementations, the process 700 can further include measuring a second capacitance charge rate of the second capacitance sensor. In some implementations, the second capacitance charge rate of the second capacitance sensor during the short duration that the second capacitance sensor is charged can be compared against a second threshold value. The second signal may be received by a controller of the electronic device. If the second capacitance charge rate is above the second threshold, then the determination at block 725 is validated. Otherwise, the process 700 can return to the initiation of the sequence at block 710, where the electronic device remains in the shelf mode.

In some implementations, the validation at block 730 can be communicated via a wireless communications component to the remote device. The remote device may provide feedback for instructing a user to proceed to additional operations for validating detection and validating activation. For example, the remote device may determine from the second sensor that the needle has punctured the skin of the body and is in proper use.

If it is determined that the electronic device is in close proximity or in contact with the body and this determination is validated at block 730, the process 700 continues to block 735. However, the validation operation at block 735 is optional. At block 735 of the process 700, the validation made at block 730 is further validated using a third signal from a third sensor. The third sensor can serve as reinforcement that the electronic device is actually in close proximity to or in contact with the body, and/or determine that a component of the electronic device is properly used or installed. In some implementations, the third sensor is a capacitive touch sensor. The third sensor can be coupled to the same sensor arrangement as the first capacitance sensor and the second capacitance sensor, or the third sensor can operate independently from the first capacitance sensor and the second capacitance sensor. In some implementations, the third sensor is located on a side of the electronic device configured to face away from the body. Where the third sensor is a capacitive touch sensor, the capacitive touch sensor is pressed for a sufficiently long duration and with sufficient force. Otherwise, the duration and force applied to the capacitive touch sensor may not be indicative of installation of the electronic device. This can avoid inadvertent activation of the device as a result of routine handling or accidental pressing of the capacitive touch sensor. In some implementations, the capacitive touch sensor is coupled to an antenna. The antenna is capable of communicating to the controller of the electronic device that the electronic device has been installed or activated. For example, the antenna may be capable of communicating to the controller of the electronic device that a detachable base has been removed. Once the electronic device has been installed or activated, other sensors of the electronic device may be activated. For example, such sensors can be activated to track the use of medication in a patient's body, thereby providing valuable information to medical personnel.

In some implementations, the validation at block 735 can be communicated via a wireless communications component to the remote device. The remote device may provide feedback for instructing a user to proceed to additional operations for validating detection and validating activation, or the remote device may indicate that the electronic device has been successfully activated. Thus, multiple sensors may be used for multiple stages of activating the electronic device. Each stage can be monitored by the remote device as the remote device provides immediate feedback to the user.

If it is determined that the electronic device is in close proximity or in contact with the body and this determination is validated at blocks 730 and 735, the process 700 continues to block 740. Otherwise, the process 700 can return to the initiation of the sequence at block 710, where the electronic device remains in the shelf mode. At block 740 of the process 700, the electronic device is caused to transition from the shelf mode to an active mode. Peripheral electronic components, a high-power clock, a low-power clock, a wireless communications component, sensors for performing detection operations of the electronic device, sensors for taking readings and/or measurements of the body, or combinations thereof may be activated during the active mode. The high-power clock and the low-power clock may operate continuously or as may be called for under the control of the controller. Thus, the full operations of the electronic device are available during the active mode.

In some implementations, the validation sequence in blocks 725, 730, and 735 can be ordered in a different manner. For example, the signal from the capacitive touch sensor can initially determine whether the electronic device is in close proximity to or in contact with the body. The signal from the capacitive touch sensor can determine if the electronic device has been installed. However, the first capacitance sensor and/or the second capacitance sensor can be used to validate if the electronic device has actually been properly installed, activated, or in use. If one or both of the first capacitance sensor and the second capacitance sensor do not validate that the electronic device is in close proximity to or in contact with the body, then the electronic device can remain in the shelf mode, and each of the sensors can return to sleep until a predetermined time interval.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the various embodiments.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

The functions in the various embodiments may be implemented in hardware, software, firmware, or any combination thereof. If implemented in software, the functions may be stored as one or more instructions or code on a non-transitory computer-readable medium or non-transitory processor-readable medium. The operations of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present disclosure is not intended to be limited to the embodiments shown herein but is to be accorded the widest scope consistent with the following claims and the principles and novel features disclosed herein.

What is claimed is:

1. An electronic device comprising:
    a first sensor, wherein the first sensor includes a first capacitance sensor;
    a second sensor, wherein the second sensor includes at least one of a capacitance sensor, an impedance sensor, an ohmic sensor, a mechanical switch, or any combination thereof;
    a housing, wherein the housing includes a circuit board and the first sensor;
    a base disposed on the housing, the base including an antenna and capable of communicating with a controller, wherein the base is capable of being detached from the housing; and
    the controller coupled to the first sensor and the second sensor, wherein the controller is configured to:
       receive a first signal from the first sensor;
       determine whether the device is in close proximity to or in contact with a body based on the first signal;
       receive, in response to determining that the device is in close proximity to or in contact with the body, a second signal from the second sensor;
       receive a third signal from the antenna indicating that the base has been detached; and
       determine whether the electronic device is activated based on the first signal, the second signal, the third signal, or any combination thereof.

2. The electronic device of claim 1, further comprising: one or more needles capable of piercing through skin of the body, wherein the one or more needles include the second sensor.

3. The electronic device of claim 2, wherein the second sensor includes a second capacitance sensor, and wherein the controller is further configured to:
    energize the one or more needles to charge the second capacitance sensor; and
    measure a rate of capacitance charge of the second capacitance sensor, wherein the second signal received from the second sensor includes the capacitance charge rate.

4. The electronic device of claim 2, wherein the one or more needles further include a subcutaneous glucose sensor capable of measuring a concentration of glucose from the body, wherein the subcutaneous glucose sensor is separate from the second sensor.

5. The electronic device of claim 1, wherein the controller is further configured to:
    energize the first sensor to charge the first capacitance sensor; and
    measure a rate of capacitance charge of the first capacitance sensor, wherein the first signal received from the first sensor includes the capacitance charge rate.

6. The electronic device of claim 1, further comprising:
    a third sensor, wherein the base includes the third sensor and the third sensor includes a capacitive touch sensor, and wherein the controller is coupled to the third sensor and further configured to:
       receive a fourth signal from the third sensor; and
       wherein determining whether the electronic device is activated is further based on the fourth signal or any combination of the first signal, the second signal, the third signal, or the fourth signal, the fourth signal indicating that the capacitive touch sensor has been pressed for a sufficient duration.

7. The electronic device of claim 1, wherein one or both of the housing and the base are rigid.

8. The electronic device of claim 1, wherein one or both of the housing and the base are semi-rigid.

9. The electronic device of claim 1, wherein one or both of the housing and the base are flexible.

10. The electronic device of claim 1, wherein the first sensor includes a first conductive surface and the second sensor includes a second conductive surface, each conductive surface being positioned on a surface of the housing configured to face the body and capable of being energized.

11. The electronic device of claim 1, wherein the controller is further configured to:
    set the electronic device to a low-power mode; and
    cause the electronic device to transition from the low-power mode to an active mode in response to determining whether the electronic device is activated.

12. The electronic device of claim 11, wherein the controller configured to set the electronic device to a low-power mode is configured to:
    deactivate a high-frequency clock associated with the electronic device, one or more peripheral electronic components in the electronic device, or any combination thereof.

13. The electronic device of claim 12, wherein the controller configured to set the electronic device to a lower-power mode is further configured to:
    energize, after a predetermined time interval, the first sensor to charge the first capacitance sensor; and
    measure a rate of capacitance charge of the first capacitance sensor, wherein the first signal received from the first sensor includes the capacitance charge rate.

14. The electronic device of claim 13, wherein the predetermined time interval is between about 1 second and about 60 seconds.

15. An electronic device comprising:
    first means for sensing proximity to or contact with a body, wherein the first sensing means includes a first capacitance sensor;
    second means for sensing proximity to or contact with a body, wherein the second sensing means includes at least one of a capacitance sensor, an impedance sensor, an ohmic sensor, a mechanical switch, or any combination thereof;
    means for housing a circuit board and the first sensor;
    means for sensing detachment of a base from a housing of the circuit board and the first sensor; and
    means for controlling the electronic device coupled to the first sensing means and the second sensing means, wherein the controlling means is configured to:
       receive a first signal from the first sensing means;
       determine whether the electronic device is in close proximity to or in contact with the body based on the first signal;

receive, in response to determining that the electronic device is in close proximity to or in contact with the body, a second signal from the second sensing means;

receive a third signal indicating detachment of the base from the housing; and determine whether the electronic device is activated based on the first signal, the second signal, the third signal, or any combination thereof.

16. The electronic device of claim 15, further comprising:
means for piercing the skin of the body, wherein the piercing means includes the second sensing means.

17. The electronic device of claim 16, wherein the second sensing means includes a second capacitance sensor, and wherein the controlling means is further configured to:

energize the piercing means to charge the second capacitance sensor; and measure a rate of capacitance charge of the second capacitance sensor, wherein the second signal received from the second sensing means includes the capacitance charge rate.

18. The electronic device of claim 15, wherein the controlling means is further configured to:

energize the first sensing means to charge the first capacitance sensor; and measure a rate of capacitance charge of the first capacitance sensor, wherein the first signal from the first sensing means includes the capacitance charge rate.

19. The electronic device of claim 15, wherein one or both of the means for housing and the base are rigid.

20. The electronic device of claim 15, wherein the first sensing means includes a first conductive surface and the second sensing means includes a second conductive surface, each conductive surface being positioned on a surface of the housing means and configured to face the body and capable of being energized.

21. A method of an electronic device in a low-power mode for determining whether the electronic device is activated, the method comprising:

receiving a first signal from a first sensor;

determining whether the electronic device is in close proximity to or in contact with a body based on the first signal;

receiving, in response to determining that the electronic device is in close proximity to or in contact with the body, a second signal from a second sensor;

receiving a third signal from an antenna indicating whether a base has been detached from a housing of the first sensor;

determining whether the electronic device is activated based on the first signal, the second signal, the third signal, or any combination thereof; and causing the electronic device to transition from a low-power mode to an active mode in response to determining that the electronic device is activated and the electronic device being in the low-power mode.

22. The method of claim 21, further comprising:
receiving a fourth signal from a third sensor; and
wherein determining whether the electronic device is activated is further based on the fourth signal or any combination of the first signal, the second signal, the third signal, or the fourth signal, wherein the electronic device is caused to transition from the low-power mode to the active mode in response to determining that the electronic device is activated and the electronic device being in the low-power mode.

23. The method of claim 21, wherein the first sensor includes a first capacitance sensor, wherein the first signal received from the first sensor includes a measurement of the rate of capacitance charge of the first capacitance sensor.

24. The method of claim 23, further comprising:
energizing, after a predetermined time interval, the first sensor to charge the first capacitance sensor; and
measuring the rate of capacitance charge of the first capacitance sensor, wherein the electronic device is determined to be in close proximity to or in contact with the body in response to the capacitance charge rate of the first capacitance sensor being greater than a threshold value.

25. The method of claim 21, further comprising:
setting the electronic device to a manufacturing mode; and
determining that a duration of time has elapsed in the manufacturing mode, wherein the electronic device is set to a low-power mode after the duration of time has elapsed.

* * * * *